(12) United States Patent
Fu

(10) Patent No.: US 8,263,823 B2
(45) Date of Patent: Sep. 11, 2012

(54) IMMUNOCOMPETENT XENOGRAFT MODEL

(75) Inventor: Yangxin Fu, Chicago, IL (US)

(73) Assignee: Adimmu Institute Inc., Hayward, CA (US)

( * ) Notice: Subject to any disclaimer, the term of this patent is extended or adjusted under 35 U.S.C. 154(b) by 630 days.

(21) Appl. No.: 12/254,776

(22) Filed: Oct. 20, 2008

(65) Prior Publication Data

US 2010/0099638 A1  Apr. 22, 2010

(51) Int. Cl.
 A01K 67/00  (2006.01)
 A61K 48/00  (2006.01)
(52) U.S. Cl. ............................ 800/8; 514/44; 424/93.1
(58) Field of Classification Search ........ 800/8; 514/44; 424/93.1
 See application file for complete search history.

(56) References Cited

U.S. PATENT DOCUMENTS

| | | | |
|---|---|---|---|
| 5,658,564 A | 8/1997 | Sykes et al. | |
| 6,060,049 A | 5/2000 | Beschorner | |
| 6,091,000 A | 7/2000 | Haynes | |
| 6,538,174 B2 | 3/2003 | Turner | |
| 6,706,947 B2 | 3/2004 | Turner | |
| 6,815,574 B2 | 11/2004 | Sawyers et al. | |
| 6,828,471 B2 | 12/2004 | Sawyers et al. | |
| 6,949,690 B2 | 9/2005 | Sawyers et al. | |
| 6,956,145 B2 | 10/2005 | Sawyers et al. | |
| 7,053,263 B2 | 5/2006 | Sawyers et al. | |
| 7,122,714 B2 | 10/2006 | Sawyers et al. | |
| 7,220,891 B2 | 5/2007 | Barsky et al. | |
| 2005/0025754 A1 | 2/2005 | Fu | |
| 2006/0294615 A1 | 12/2006 | Lin | |
| 2007/0006331 A1 | 1/2007 | Sawyers et al. | |
| 2007/0202106 A1* | 8/2007 | Palucka et al. ............. | 424/145.1 |

FOREIGN PATENT DOCUMENTS

WO  WO 2008/098183  8/2008

OTHER PUBLICATIONS

Berney et al (Transplantation, 72: 133-14, 2001).*
Gorldrath et al (Immunity, 11: 183-190, 1999).*
Perryman et al (Vet Pathol, 41:95-100, 2004).*
Taconic.com-NIH nude rats.*
Taconic.com-NOD-scid mice.*
International Search Report for PCT/US2008/011963, Jun. 25, 2009, Yangxin Fu.
Apetoh, L., et al., The Interaction Between HMGB1 and TLR4 Dictates the Outcome of Anticancer Chemotherapy and Radiotherapy, *Immunol Rev*, Dec. 2007,220, 47-59.
Blank, C., et al., PD-L1/B7H-1 Inhibits the Effector Phase of Tumor Rejection by T Cell Receptor (TCR) Transgenic CD8+ T Cells, *Cancer Res*, Feb. 1, 2004, 64(3), 1140-1145.
Boon, T., et al., Human Tumor Antigens Recognized by T Lymphocytes, *J Exp Med*, Mar. 1, 1996, 183(3), 725-729.
Brown, J.M., et al., High-Dose Single-Fraction Radiotherapy: Exploiting a new Biology?, *Int J Radiat Oncol Biol Phys*, Jun. 2008, 71(2), 324-325.
Browning, J.L., et al., Lymphotoxin β, a Novel Member of the TNF Family That Forms a Heteromeric Complex with Lymphotoxin on the Cell Surface, Cell, Mar. 26, 1993, 72, 847-856.
Bui, J.D., et al., Cancer Immunosurveillance, Immunoediting and Inflammation: Independent or Interdependent Processes?, *Curr Opin Immunol*, Apr. 2007, 19(2), 203-208.
Chakraborty, M., et al., External Beam Radiation of Tumors Alters Phenotype of Tumor Cells to Render Them Susceptible to Vaccine-Mediated T-Cell Killing, *Cancer Res*, Jun. 15, 2004, 64, 4328-4337.
Chang, B.K., et al., Stereotactic Body Radiation Therapy: A Comprehensive Review, *Am J Clin Oncol*, Dec. 2007, 30(6), 637-644.
Clemente, C.G., et al., Prognostic Value of Tumor Infiltrating Lymphocytes in the Vertical Growth Phase of Primary Cutaneous Melanoma, *Cancer*, Apr. 1, 1996, 77(7), 1303-1310.
Clynes, R.A., et al., Inhibitory Fc Receptors Modulate In Vivo Cytoxicity Against Tumor Targets, *Nat Med*, Apr. 2000, 6(4), 443-446.
Devos, T., et al., Role of CD4+ and CD8+ T Cells in Rejection of Hear or Islet Xenografts in Recipients With Xenotolerance in the Innate Immune Compartment, *Transplantation Proceedings*, Jan. 2005, 37(1), 516-517.
Dunn, G.P., et al., The Immunobiology of Cancer Immunosurveillance and Immunoediting, *Immunity*, Aug. 2004, 21(2), 137-148.
Ercolini, A.M., et al., Recruitment of Latent Pools of High-Avidity CD8+ T Cells to the Antitumor Immune Response, *J Exp Med*, May 16, 2005, 201(10), 1591-1602.
Fang, H.B., et al., Hierarchical Models for Tumor Xenograft Experiments in Drug Development, *J Biopharm Stat*, Nov. 2004, 14 (4), 931-945.
Garcia-Barros, M., et al., Tumor Response to Radiotherapy Regulated by Endothelial Cell Apoptosis, *Science*, May 16, 2003, 300(5622), 1155-1159.
Gattinoni, L., et al., Adoptive Immunotherapy for Cancer: Building on Success, *Nat Rev Immunol*, May 2006, 6(5), 383-393.

(Continued)

*Primary Examiner* — Gerald Leffers, Jr.
*Assistant Examiner* — Magdalene Sgagias
(74) *Attorney, Agent, or Firm* — Jun He Law Offices P.C.; James J. Zhu

(57) ABSTRACT

The teachings are directed to an immunocompetent xenograft model. The model comprises an immunodeficient animal modified to have a reconstituted immune system, wherein a xenograft is transplanted in the animal and allowed to establish for an establishment period of at least about 10 days. The xenograft simulates a tissue in a subject in need of a treatment. In these embodiments, the reconstituted immune system is created after the establishment period, and is created by administering a total number of T-cells to the animal. The total number of T-cells consists of a preselected number of responsive T-cells, a preselected number of non-responsive T-cells, and a preselected ratio of responsive T-cells to total T-cells. The preselected number of responsive T-cells simulates a number of responsive T-cells in the subject, and the ratio of the number of responsive T-cells to total T-cells ranges from about 1:100,000 to about 30:100,000.

16 Claims, 14 Drawing Sheets

OTHER PUBLICATIONS

Hatfield, P., et al., Radiation-Induced Cell Death and Dendritic Cells: Potential for Cancer Immunotherapy?, *Clin Oncol (R Coll Radiol)*, Feb. 2005, 17(1), 1-11.

Kiessling, R., et al., Cellular Immunity to the Her-2/neu Protooncogene, *Adv Cancer Res*,2002, 85, 101-144.

Kono, K., et al., Trastuzumab (Herceptin) Enhances Class I-Restricted Antigen Presentation Recognized by HER-2/neu-Specific T Cytotoxic Lymphocytes, *Clin Cancer Res*, Apr. 1, 2004, 10, 2538-2544.

Liao, Y. P., et al., Ionizing Radiation Affects Human MART-1 Melanoma Antigen Processing and Presentation by Dendritic Cells, *J Immunol*, Aug. 15, 2004, 173(4), 2462-2469.

Lowenthal, J.W., et al., Activation of Mouse Lymphocytes Inhibits Induction of Rapid Cell Death by X-Irradiation, *J Immunol* , Aug. 1985, 135(2), 1119-1125.

Lugade, A.A., et al., Local Radiation Therapy of B16 Melanoma Tumors Increases the Generation of Tumor Antigen-Specific Effector Cells that Traffic to the Tumor, *J Immunol*, Jun. 15, 2005, 174(12), 7516-7523.

Lutz, M.B., et al., An Advanced Culture Method for Generating Large Quantities of Highly Pure Dendritic Cells From Mouse Bone Marrow, *J Immunol Methods*, Feb. 1, 1999, 223(1), 77-92.

Miller, F.R., et al., Invasion Metastasis, 1983, 3, 22-31.

Moon, J.J., et al., Naive $CD4^+$ T Cell Frequency Varies for Different Epitopes and Predicts Repertoire Diversity and Response Magnitude, *Immunity*, Aug. 2007, 27(2), 203-213.

Norihisa, Y., et al., Stereotactic Body Radiotherapy for Oligometastatic Lung Tumors, *Int J Radiat Oncol Biol Phys*, Oct. 1, 2008, 72(2), 398-403.

North, R.J., Radiation-Induced, Immunologically Mediated Regression of an Established Tumor as an Example of Successful Therapeutic Immunomanipulation Preferential Elimination of Suppressor T Cells Allows Sustained Production of Effector T Cells, *J Exp Med*, Nov. 1, 1986, 164(5), 1652-1666.

Ostrand-Rosenberg, S., Animal Models of Tumor Immunity, Immunotherapy and Cancer Vaccines, *Curr Opin Immunol*, Apr. 2004, 16(2), 143-150.

Papiez, L., et al., Hypofractionation in Radiation Therapy and its Impact, *Med Phys*, Jan. 2008, 35(1), 112-118.

Piccart-Gebhart, M.J., et al. Trastuzumab After Adjuvant Chemotherapy in HER2-Positive Breast Cancer, *N Engl J Med*, Oct. 20, 2005, 353(16), 1659-1672.

Pulaski, B.A., et al., Unit 20.2 Mouse 4T1 Breast Tumor Model, *Curr Protoc Immunol*, 2000, 20.2.1-20.2.16.

Reits, E. A., et al., Radiation Modulates the Peptide Repertoire, Enhances MHC Class I Expression, and Induces Successful Antitumor Immunotherapy, *J Exp Med*, May 15, 2006, 203(5), 1259-1271.

Romond, E.H., et al., Trastuzumab Plus Adjuvant Chemotherapy for Operable HER2-Positive Breast Cancer, *N Engl J Med*, Oct. 20, 2005, 353(16), 1673-1684.

Rosenberg, S.A., The Emergence of Modern Cancer Immunotherapy, *Ann Surg Oncol*, May 2005,12(5), 344-346.

Salama, J.K., et al., An Initial Report of a Radiation Dose-Escalation Trial in Patients With One to Five Sites of Metastatic Disease, *Clin Cancer Res*, Aug. 15, 2008, 14(16), 5255-5259.

Schreiber, H., Tumor Immunology, Fundamental Immunology, W. E. Paul, ed. (New York, Lippincott Raven Press), 1999, 1237-1270.

Shultz, L. D., et al., Humanized Mice in Translational Biomedical Research, *Nat Rev Immunol*, Feb. 2007, 7, 118-130.

Sjoblom, T., et al., The Consensus Coding Sequences of Human Breast and Colorectal Cancers, *Science*, Oct. 13, 2006, 314(5797), 268-274.

Strowig, T., et al., Priming of Protective T Cell Responses Against Virus-Induced Tumors in Mice With Human Immune System Components, *J Exp Med*, Jun. 8, 2009, 206(6), 1423-1434.

Suggitt, M., et al., 50 Years of Preclinical Anticancer Drug Screening: Empirical to Target-Driven Approaches, *Clin Cancer Res*, Feb. 1, 2005, 11, 971-981.

Turk, M.J., et al., Concomitant Tumor Immunity to a Poorly Immunogenic Melanoma is Prevented by Regulatory T Cells, *J Exp Med*, Sep. 20, 2004, 200(6), 771-782.

Wasserman, J., et al., Immunosuppression in Irradiated Breast Cancer Patients: In Vitro Effect of Cyclooxygenase Inhibitors, *Bull N Y Acad Med*, Jan. 1989, 65(1), 36-44.

Wood, L.D., et al., The Genomic Landscapes of Human Breast and Colorectal Cancers, *Science*, Nov. 16, 2007, 318(5853), 1108-1113.

Yu, P., et al., Priming of Naive T Cells Inside Tumors Leads to Eradication of Established Tumors, *Nat Immunol*, Feb. 2004, 5(2), 141-9.

Yu, P., et al., The Role of Stroma in Immune Recognition and Destruction of Well-Established Solid Tumors, *Curr Opin Immunol*, Apr. 2006, 18(2), 226-231.

Yu, P., et al., Targeting the Primary Tumor to Generate CTL for the Effective Eradication of Spontaneous Metastases, *J Immunol*, 2007, 179, 1960-1968.

Zhang, L., et al., Intratumoral T Cells, Recurrence, and Survival in Epithelial Ovarian Cancer, *N End J Med*, 2003, 348, 203-213.

Chemotherapy, Non-Hodgkin's Lymphoma Cyberfamily, [online] [retrieved on Nov. 16, 2008] URL: http://www.nhlcyberfamily.org/treatments/chemotherapy.htm.

HealthDigest.org: Medical, Drug, and Health Library, Dacarbazine Dosage, Interactions, Side Effects, How to Use, [online] [retrieved on Oct. 16, 2008] URL: http://www.healthdigest.org/topics/category/1126-dacarbazine-dosage-interactions-side-effects-how-to-use.

OncoLink: Abramson Cancer Center of the University of Pennsylvania, Cancer Treatment Information: Chemotheray Primer, [online] [retrieved on Oct. 16, 2008] URL: http://www.oncolink.org/treatment/article.cfm?c=2&s=9&id=224.

Rx List: The Internet Drug Index, Adriamycin PFS, [online] [retrieved on Oct. 16, 2008] URL: http://www.rxlist.com/adriamycin-pfs-drug.htm#ids.

Rx List: The Internet Drug Index, Taxol, [online] [retrieved on Oct. 16, 2008] URL: http://www.rxlist.com/taxol-drug.htm#ids.

* cited by examiner

IMMUNOCOMPETENT XENOGRAFT MODEL

BACKGROUND

1. Field of the Invention

The teachings describe an immunocompetent xenograft model for testing methods of treating a tissue in a live subject.

2. Description of Related Art

Animal models are needed in the development and evaluation of current or innovative therapeutics, such as cancer therapies. In fact, human tumor xenograft models are the mainstay of preclinical proof-of-concept testing of all experimental anti-tumor drugs.

Animal models have been in development since the 1950s and have gone through several stages of improvements from mouse tumors to human xenografts in immunodeficient mice, to transgenic mice, and then to humanized mice. An increasing amount of evidence suggests, however, that immune responses may contribute to the efficacy of some therapies, such as therapies directed to cancer management. Unfortunately, it has been very difficult to study the role of immune responses in treatments, such as in the treatment of human cancer in preclinical studies, since the rejection of human tumors in immunocompetent mouse models remains a problem.

Current models, for example, use immunodeficient xenograft models to test drug treatments, radiation treatments, and the combination of drugs and radiation therapy. As such, these current xenograft models do not simulate immune response conditions and could readily provide an incorrect assessment of the efficacy of a treatment, resulting in medical research and development programs, and funding, that reject treatments that should be further studied and accept treatments that should be rejected. Federal regulation of drugs, for example, most often naturally follow suit. Given the large expense involved in developing new treatments, whether the treatment use a new drug, old drug, radiation therapy, combination therapy, or the like, one of skill in the art will appreciate a novel, immunocompetent xenograft model that takes into account the contribution of the immune system to the efficacy of a treatment regime.

SUMMARY OF THE INVENTION

As described above, the teachings provided herein are generally directed to an immunocompetent xenograft model for testing methods of treating a tissue in a live subject. One of skill will appreciate that the concepts supported through these teachings are not limited to the scope of the writings. Numerous applications will become apparent through the disclosures provided herein.

In some embodiments, the teachings are directed to an immunocompetent xenograft model. The model comprises an immunodeficient animal modified to have a reconstituted immune system, wherein a xenograft is transplanted in the animal and allowed to establish for an establishment period of at least about 10 days. The xenograft simulates a tissue in a subject in need of a treatment. In these embodiments, the reconstituted immune system is created after the establishment period, and is created by administering a total number of T-cells to the animal. The total number of T-cells consists of a preselected number of responsive T-cells, a preselected number of non-responsive T-cells, and a preselected ratio of responsive T-cells to total T-cells. The preselected number of responsive T-cells simulates a number of responsive T-cells in the subject, and the ratio of the number of responsive T-cells to total T-cells ranges from about 1:100,000 to about 30:100,000.

The animal can be chosen for a particular type of testing, for example. In some embodiments, the animal can be a mammal or a transgenic variation thereof. In these embodiments, the animal can be a primate species, a ruminant species, or a transgenic variation thereof. In some embodiments, the animal can be a rat, dog, cat, macaque, marmoset, spider monkey, squirrel monkey, baboon, chimpanzee, rabbit, pig, goat, cow, horse, sheep, deer guinea pig, hamster, gerbil, owl, llama, or a transgenic variation thereof. In some embodiments, the animal can be a mouse and, in these embodiments, the mouse can be an immunodeficient mouse such as, for example, a Rag-1 immunodeficient mouse or a C57BL/6 mouse.

The xenograft model can be used to simulate the response of a variety of tissues to a treatment in a subject. In some embodiments, the xenograft can simulate a solid cancer or a liquid cancer in the subject. In some embodiments, the xenograft comprises a cancer tissue selected from the group consisting of breast cancer, lung cancer, prostate cancer, colon cancer, renal cancer, liver cancer, leukemia, lymphoma, and skin cancer. In some embodiments, the xenograft comprises a donor tissue. In some embodiments, the donor tissue can be selected from the group consisting of heart tissue, lung tissue, kidney tissue, liver tissue, pancreas tissue, intestinal tissue, hand tissue, cornea tissue, skin graft tissue, penis tissue, blood vessel tissue, and bone tissue.

As described above, the reconstituted immune system is created after the establishment period and, in some embodiments, the establishment period can range from about 2 weeks to about 4 weeks. And, in some embodiments, the establishment period can be about 3 weeks.

Also, as described above, the reconstituted immune system is created by administering a total number of T-cells to the animal, wherein the T-cells include responsive T-cells and non-responsive T-cells. In some embodiments, the number of responsive T-cells ranges from about 50 to about 5000, from about 200 to about 2000, or any range therein. And, in some embodiments, the ratio of responsive T-cells to total T-cells ranges from about 1:100,000 to about 10:100,000. In some embodiments, the T-cells can comprise T-cells from a transgenic mouse such as, for example, T-cells from a transgenic TCR mouse including, but not limited to, T-cells can comprise T-cells from an OT-1 transgenic TCR mouse. In some embodiments, the T-cells comprise CD8+ 2C transgenic T-cells. The T-cells, in many embodiments, are activated by the therapy, and the therapy can include, for example, radiation therapy.

The teachings are also directed to a method of producing the immunocompetent xenograft model. In some embodiments, the method comprises transplanting a xenograft in an immunodeficient animal. In these embodiments, the method includes allowing the xenograft to establish in the animal for an establishment period of at least about 10 days and creating a reconstituted immune system. The creating of the reconstituted immune system comprises administering a total number of T cells to the animal, wherein the total number of T-cells consists of a preselected number of responsive T-cells, a preselected number of non-responsive T-cells, and a preselected ratio of responsive T-cells to total T-cells. The preselected number of responsive T-cells simulates the number of responsive T-cells in the subject, and the ratio of the number responsive T-cells to total T-cells ranging from about 1:100,000 to about 30:100,000.

The teachings are also directed to an assay for testing the efficacy of a treatment of a tissue. In some embodiments, the assay comprises administering a treatment to the immunocompetent xenograft model, described above, to treat a tissue. In these embodiments, the assay also includes measuring the effect of the treatment on the tissue. In some embodiments, the treatment includes radiation therapy, chemotherapy, antibody therapy, immunotherapy, or any combination thereof.

The teachings are also directed to a method of treating a cancer. In some embodiments, the method comprises administering an agent to a subject in need of a cancer treatment, wherein the dose of the agent is selected to reduce or eliminate an immunosuppression that would otherwise occur when administering a substantially higher dose of the agent in the subject; and administering radiation therapy in combination with the agent, wherein the reduction or elimination of the immunosuppression enhances the efficacy of the radiation therapy when compared to the efficacy of the radiation therapy otherwise observed when administered in combination with the substantially higher dose of the agent in the subject. In some embodiments, the agent comprises one or more chemotherapeutic agents. In these embodiments, the agent can be selected from the group consisting of dacarbazine, paclitaxel, doxorubicin.

In some embodiments, the radiation therapy can be administered in a single, localized high-dose ranging from about 20 Gy to about 100 Gy. In some embodiments, the radiation therapy can be administered in a total dose ranging from about 20 Gy to about 100 Gy using a modified hypofractionation regime of dosing comprising from about 2 doses to about 5 doses during a time frame of one week. In some embodiments, the radiation therapy can be administered in a total dose ranging from about 20 Gy to about 100 Gy using a modified hypofractionation regime of dosing comprising from 2 doses to 3 doses during a time frame ranging from about 2 days to about 3 days. The radiation therapy can also be administered in a total dose ranging from about 45 Gy to about 60 Gy using a modified hypofractionation regime of dosing comprising administering a single dose ranging from about 15 Gy to about 20 Gy for each day during a 3-day time frame.

The method can be used to treat a variety of cancers. In some embodiments, the cancer is resistant to radiation therapy in immunodeficient xenograft models. In some embodiments, the cancer comprises a cancer tissue selected from the group consisting of breast cancer, lung cancer, prostate cancer, colon cancer, renal cancer, liver cancer, leukemia, and skin cancer.

DETAILED DESCRIPTION

Figure 1:
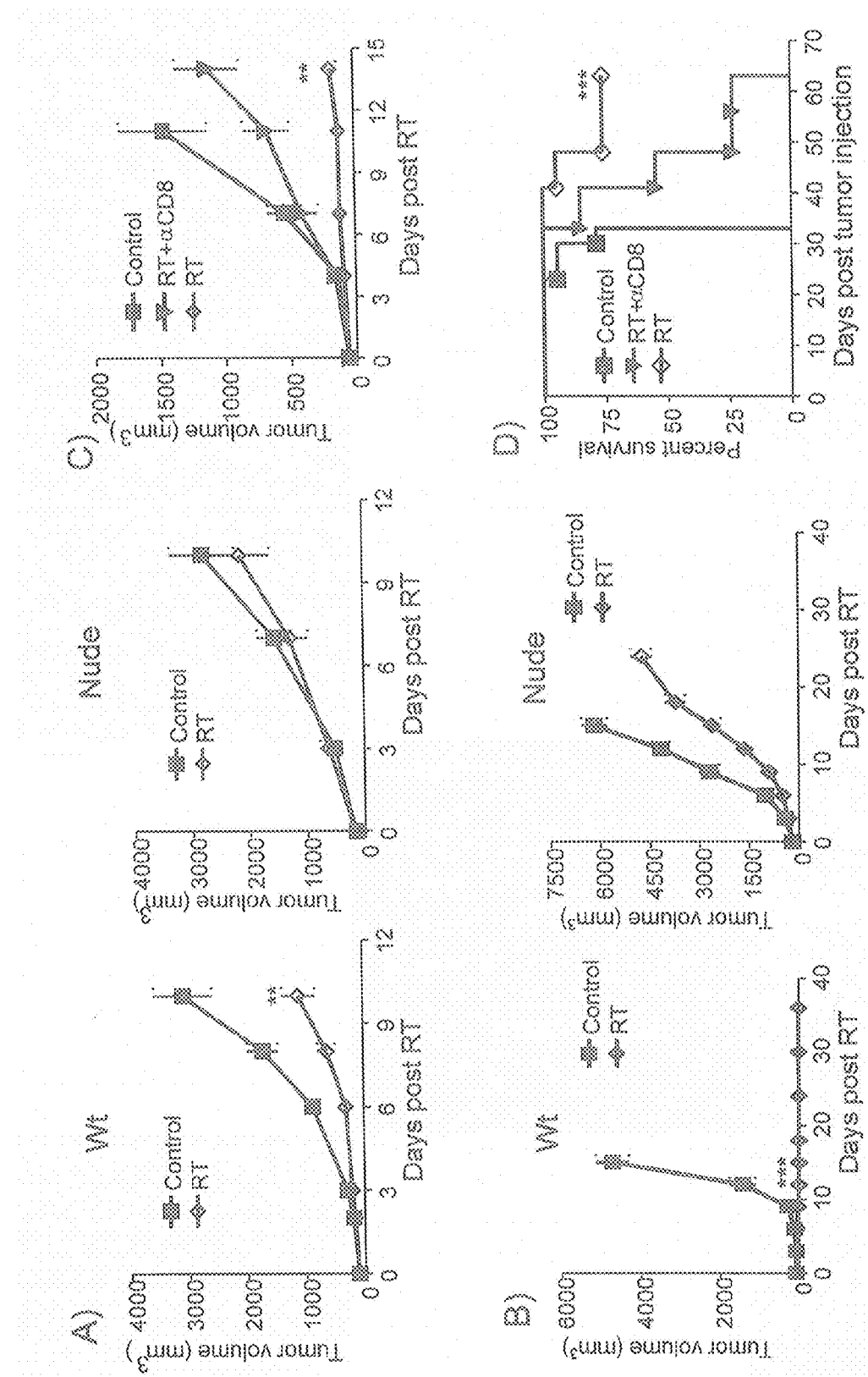
FIGS. 1A through 1D show that immune-deficient mice having a poorly immunogenic tumor are more resistant to radiation therapy than immunocompetent mice, according to some embodiments.

The teachings generally describe an immunocompetent xenograft model for testing methods of treating a tissue in a live subject. The problem of current xenograft models is recognized, and a solution to the long-felt and unsolved need for an immunocompetent xenograft model to evaluate therapies is provided. One of skill will appreciate having a model that simulates immune response contributions to therapies, particularly where immune response is found to play a role in treatment efficacy.

Current xenograft models, for example, are used in assays based on immunodeficient mice for preclinical testing of drug treatments, radiation treatments, and the combination of drugs and radiation on human tissue. These models do not simulate actual conditions that include the contribution of immune responses to treatments. The teachings provided herein show that the presence or absence of an immune response can seriously alter the efficacy of treatments, such as treatments with anti-tumor drugs that include, but are not limited to, chemotherapy drugs and immunotherapy drugs.

The central problem to overcome in developing an immunocompetent xenograft model is the rejection of the xenograft tissue by the model. A solution to the problem includes developing a method of reconstituting an immune system in an otherwise immunodeficient animal, wherein the immune system does not reject the xenograft.

Without intending to be bound by any theory or mechanism of action, the art has taught that there are at least 80 mutated antigens per growing tumor, some of which can be presented to T-cells in the patient. See Sjoblom, T. et al. Science 314, 268-274(2006); and, Wood, L. D. et al. Science 318, 1108-1113(2007). And, each antigenic epitope has about 20 to about 200 specific T-cells per host. See Moon, J. J. et al. Immunity 27, 203-213(2007). As such, there are about 300 to about 3000 tumor reactive T-cells in an immunocompetent host. Unfortunately, simply transferring such small numbers of T-cells into immunodeficient mice, such as Rag-1 −/− mice, has been shown to result in a rapid homeostatic proliferation of reactive T-cells that artificially activates the T-cells and in a response that ultimately rejects the xenograft.

Surprisingly, a method of reconstituting an immune system in an immune-deficient animal has been discovered, wherein the immunocompetent animal does not reject the xenograft. The method comprises transplanting a xenograft in an immunodeficient animal and allowing the xenograft to establish in the animal for an establishment period before creating a reconstituted immune system.

A tissue, whether a donor tissue or a cancer tissue, can be considered "established" after it has been given an appropriate amount of time to develop in the animal after inoculation of the tissue into the animal. The time allowed for the tissue for developing in the animal can be referred to as an "establishment time." In some embodiments, the establishment time is at least 3 days, 5 days, 7 days, 10 days, 2 weeks, 3 weeks, 4 weeks, or any range therein, after inoculation of the tissue. In some embodiments, the tissue can be considered to be "established" after it has developed into a tissue having a size ranging from about 100 mm$^3$ to about 300 mm$^3$. In some embodiment, the tissue can be considered to be "established" after it has developed into a tissue having a size ranging from about 50 mm$^3$ to about 500 mm$^3$, from about 125 mm$^3$ to about 250 mm$^3$, from about 75 mm$^3$ to about 400 mm$^3$, or any range therein.

The creating of the reconstituted immune system comprises administering a total number of T cells to the animal, wherein the total number of T-cells consists of a preselected number of responsive T-cells, a preselected number of non-responsive T-cells, and a preselected ratio of responsive T-cells to total T-cells. The preselected number of responsive T-cells simulates the number of responsive T-cells in the subject, and the ratio of the number responsive T-cells to total T-cells ranging from about 1:100,000 to about 30:100,000.

Also, as described above, the reconstituted immune system is created by administering a total number of T-cells to the animal, wherein the T-cells include responsive T-cells and non-responsive T-cells. In some embodiments, the total number of responsive T-cells should range from about 200 to about 3000 per mouse for an established tumor. In some embodiments, the total number of tumor cells should range from about 50 to about 5000, from about 100 to about 4000, from about 200 to about 3500, from about 200 to about 2000, from about 300 to about 3000, or any range therein.

In some embodiments, the total transfer of T-cells should range from about 1 million to about 3 million. In some embodiments, the total transfer of T-cells should range from about 0.5 million to about 5 million, from about 1.75 million to about 3.5 million, or any range therein, to prevent homeostasis proliferation of tumor reactive T cells. And, in some embodiments, the ratio of responsive T-cells to total T-cells ranges from about 1:100,000 to about 10:100,000.

In some embodiments, the T-cells can comprise T-cells from a transgenic mouse such as, for example, T-cells from a transgenic TCR mouse including, but not limited to, T-cells can comprise T-cells from an OT-1 transgenic TCR mouse. In some embodiments, the T-cells comprise CD8+ 2C transgenic T-cells. The T-cells, in many embodiments, are activated by the therapy, and the therapy can include, for example, radiation therapy.

The animal can be chosen for a particular application, for example, and can be any suitable animal known to one of skill for the particular application. In some embodiments, the animal can be a mammal or a transgenic variation thereof. In these embodiments, the animal can be a primate species, a ruminant species, or a transgenic variation thereof. In some embodiments, the animal can be a rat, dog, cat, macaque, marmoset, spider monkey, squirrel monkey, baboon, chimpanzee, rabbit, pig, goat, cow, horse, sheep, deer guinea pig, hamster, gerbil, owl, llama, or a transgenic variation thereof. In some embodiments, the animal can be a mouse and, in these embodiments, the mouse can be an immunodeficient mouse such as, for example, a Rag-1 immunodeficient mouse or a C57BL/6 mouse.

The xenograft model can be used to simulate the response of a variety of tissues to a treatment in a subject. In some embodiments, the xenograft can simulate a solid cancer or a liquid cancer in the subject. In some embodiments, the xenograft comprises a cancer tissue selected from the group consisting of breast cancer, lung cancer, prostate cancer, colon cancer, renal cancer, liver cancer, leukemia, lymphoma, and skin cancer. In some embodiments, the xenograft comprises a donor tissue to simulate a tissue or an organ transplant. In some embodiments, the donor tissue can be selected from the group consisting of heart tissue, lung tissue, kidney tissue, liver tissue, pancreas tissue, intestinal tissue, hand tissue, cornea tissue, skin graft tissue, penis tissue, blood vessel tissue, and bone tissue.

The teachings are also directed to an assay for testing the efficacy of a treatment of a tissue. In some embodiments, the assay comprises administering a treatment to the immunocompetent xenograft model, described above, to treat a tissue. In some embodiments, the treatment includes radiation therapy, chemotherapy, immunotherapy, or a combination thereof. In these embodiments, the assay also includes measuring the effect of the treatment on the tissue. Measuring methods can include any technique known to one of skill, including, but not limited, the measurement of the reduction of the size of a tumor, symptoms and measures of transplant rejection, and the like.

It has been discovered that high doses of first agent can cause an immunosuppression in a subject that reduces the effectiveness of a second agent. As such, the teachings provided herein are also directed to a method of treating cancer using a controlled combination administration of agents. In some embodiments, the method comprises administering a first agent in an amount that reduces or eliminates immunosuppression and administering a second agent. In some embodiments, the method comprises administering a controlled dose of a chemotherapeutic agent in combination with radiation therapy. In some embodiments, the method comprises administering a combination of a low total dose of chemotherapy in combination with radiation therapy. In some embodiments, the method comprises administering a combination of a series of low fractionated doses of a chemotherapeutic agent in combination with radiation therapy. A dose of an agent, for example a first agent, is considered "substantially higher," in some embodiments, where the immunosuppression created by the dose is to an extent that reduces the efficacy of a second agent that is administered in combination with the first agent. In some embodiments, the first agent and second agent can be any combination of a chemotherapeutic agent, and the second agent can be an immunotherapy agent, an antibody, radiation, a tumor-necrosis factor, or a chemotherapeutic agent, for example.

In some embodiments, the method comprises administering an agent to a subject in need of a cancer treatment, wherein the dose of the agent is selected to reduce or eliminate an immunosuppression that would otherwise occur when administering a substantially higher dose of the agent in the subject; and administering radiation therapy in combination with the agent, wherein the reduction or elimination of the immunosuppression enhances the efficacy of the radiation therapy when compared to the efficacy of the radiation therapy otherwise observed when administered in combination with the substantially higher dose of the agent in the subject. In some embodiments, the agent comprises one or more chemotherapeutic agents. In these embodiments, the agent can be selected, for example, from the group consisting of dacarbazine, paclitaxel, doxorubicin.

In some embodiments, lower doses of chemotherapy are used in combination with the radiation therapy in order to avoid or reduce the immunosuppression and enhance the efficacy of the radiation therapy. In these embodiments, the chemotherapy can be administered in a dose that ranges, for example, from about 0.01 mg/kg to about 50 mg/kg, from about 0.01 mg/kg to about 40 mg/kg, from about 0.01 mg/kg to about 30 mg/kg, from about 0.01 mg/kg to about 20 mg/kg, from about 0.1 mg/kg to about 10 mg/kg, from about 0.1 mg/kg to about 50 mg/kg, from about 0.1 mg/kg to about 30 mg/kg, from about 0.1 mg/kg to about 10 mg/kg, from about 0.3 mg/kg to about 3 mg/kg, from about 0.2 mg/kg to about 2 mg/kg, from about 0.1 mg/kg to about 1 mg/kg, from about 0.05 mg/kg to about 0.5 mg/kg, or any range therein.

In some embodiments, the radiation therapy can be administered in a single, localized high-dose ranging from about 20 Gy to about 100 Gy. In some embodiments, the radiation therapy can be administered in a total dose ranging from about 20 Gy to about 100 Gy using a modified hypofractionation regime of dosing comprising from about 2 doses to about 5 doses during a time frame of one week. In some embodiments, the radiation therapy can be administered in a total dose ranging from about 20 Gy to about 100 Gy using a modified hypofractionation regime of dosing comprising from 2 doses to 3 doses during a time frame ranging from about 2 days to about 3 days. The radiation therapy can also be administered in a total dose ranging from about 45 Gy to about 60 Gy using a modified hypofractionation regime of dosing comprising administering a single dose ranging from about 15 Gy to about 20 Gy for each day during a 3-day time frame.

The method can be used to treat a variety of cancers. In some embodiments, the cancer is resistant to radiation therapy when treated in immunodeficient xenograft models. In some embodiments, the cancer comprises a cancer tissue selected from the group consisting of breast cancer, lung cancer, prostate cancer, colon cancer, renal cancer, liver cancer, leukemia, and skin cancer.

The radiation can be administered in any form known to one of skill in the art of radiation therapy including for example, any form of ionizing radiation. In some embodiments, the radiation is from a cobalt source, an x-ray source, or a combination thereof. In some embodiments, the radiation therapy includes external beam radiotherapy (EBRT or XBRT), brachytherapy, and unsealed source radiotherapy. Examples of external beam therapy include, for example, x-ray therapy, cobalt, and proton therapy. In some embodiments, the dose of radiation can be a single dose, a single low dose, a single high dose, a hypofractionated dose, a hyperfractionated dose, or any other dosage regime known to one of skill. In some embodiments, the dose is administered in few fractions (hypofractionated) to reduce the immunosuppressive effects of the radiation. The dose can be administered, for example, in less than 6 fractions, less than 4 fractions, or in less than 3 fractions. One of skill will be able to select the appropriate dose for the condition to be treated, taking into account all patient variables.

The amount of radiation used in radiation therapy depends on the type and stage of cancer being treated. In some embodiments, a curative diseases, such as a solid epithelial tumor, for example, can have total doses that range from about 60 Gy to about 80 Gy. In some embodiments, such as lymphoma tumors, total doses can range from about 80 Gy to about 100 Gy.

Preventative, or adjuvant, doses can be administered in total doses ranging from about 45 Gy to about 60 Gy using fractionation doses ranging from about 1.8 Gy to about 2.0 Gy. Such doses can apply, for example, to breast, head, and neck cancers. One of skill will appreciate that dosing can depend, for example, on any of a variety of factors, such as whether the patient is receiving other therapies in combination with the radiation therapy. Other therapies can include, but are not limited to, chemotherapy. One of skill may also consider whether the radiation therapy is being administered in combination with surgery, such as before or after surgery, and the degree of success of surgery.

As can be seen, the total dose of radiation can be fractionated into smaller doses that are spread out over time to give normal cells that are also exposed to the radiation some time to recover. Fractionation regimes differ highly between treatment centers and physicians. In some embodiments, the fractionation schedule for adults may include administration of about 1.8 Gy/day to about to 2.0 Gy/day, five days a week. In some embodiments, the fractionation schedule may include administration of about 2.67 Gy/day to 2.75 Gy/day. In some embodiments, such as with children, the fractionation schedule can range from about 1.5 Gy/day to about 1.7 Gy/day, as a low dose to reduce the chance and severity of potential late-onset side effects.

In some embodiments, hyperfractionation can be used, where two fractions per day are administered near the end of a course of treatment. These embodiments can be used on tumors that regenerate faster when they're smaller such as, for example, some head and neck tumors known to those of skill. In some embodiments, a continuous hyperfractionated accelerated radiotherapy (CHART) is used and consists of three smaller fractions per day. CHART can be administered to treat lung cancer, for example. In some embodiments, radiation implants are used. In these embodiments, the implants can administer radiation that is fractionated over minutes or hours, or they can be permanent seeds which slowly deliver radiation until they become inactive.

In some embodiments, the radiation therapy can be administered in doses ranging from about 1.0 Gy to about 100 Gy, from about 1.0 Gy to about 90 Gy, from about 1.0 Gy to about 80 Gy, from about 1.0 Gy to about 70 Gy, from about 1.0 Gy to about 60 Gy, from about 1.0 Gy to about 50 Gy, from about 1.0 Gy to about 40 Gy, from about 1.0 Gy to about 30 Gy, from about 1.0 Gy to about 20 Gy, from about 1.0 Gy to about 15 Gy, from about 1.5 Gy to about 15 Gy, from about 2 Gy to about 10 Gy, from about 2 Gy to about 7 Gy, or any range therein. And, as described, the radiation can be administered in a single dose or in fractionated doses. The fractionated doses can include, for example, hyperfractionated radiation therapy, hypofractionated radiation therapy (HFRT), conventionally fractionated radiation therapy (CFRT), stereotactic body radiation therapy (SBRT), or modified forms thereof. In many embodiments, the dose of radiation is administered locally.

Surprisingly, the immunocompetent xenograft models taught herein have shown that hypofractionated, modified hypofractionated, and single dose administrations of radiation therapy can stimulate the immune system, whereas conventional or hyperfractionated radiation therapy can induce immunosuppression. While not intending to be bound by any theory or mechanism of action, it is believed that the repeated administration of radiation results in a repeated killing of immune cells that migrate into the tumor tissues.

As such, a smaller number of radiation doses can be used in an attempt to stimulate the immune system. In some embodiments, a single dose of radiation is used, and the single dose can be in an amount used in stereotactic body radiation therapy. In some embodiments, a hypofractionated dose of radiation is used, where the radiation is administered at a frequency 5 times or more per week for about 2 weeks to about 3 weeks. In some embodiments, a hypofractionated dose of radiation is used, where the radiation is administered at a frequency of less than 5 times for about two weeks and a high dose of radiation is administered during each administration. In some embodiments, a hypofractionated dose of radiation is used, where the radiation is administered at a modified frequency that ranges from about 1 dose to about 7 doses, from about 1 dose to about 5 doses, from about 1 dose to about 3 doses, from 2 doses to 3 doses, or any range therein.

Agents and Methods of Administration

The agents that can be used in the teachings provided herein include any agent contemplated by one of skill and include compositions that can provide a therapeutic and/or prophylactic effect in the treatment of a disease, or ameliorization of one or more symptoms of a disease in a subject. The term "subject" and "patient" can be used interchangeably and refer to an animal such as a mammal including, but not limited to, non-primates such as, for example, a cow, pig, horse, cat, dog, rat and mouse; and primates such as, for example, a monkey or a human. The term "treating" can refer to the administering one or more therapeutic or prophylactic agents taught herein.

A variety of agents can be used in the teachings provided herein. For example, the agents may include any bioactive agent, such as a chemotherapeutic agent, an immunotherapeutic agent, an antibody, a tumor-necrosis factor, a source of radiation, and the like. In some embodiments, the methods further comprise the co-administration of a second active agent. The bioactive agents can be any moiety capable of contributing to a therapeutic effect, a prophylactic effect, both a therapeutic and prophylactic effect, or other biologically active effect in a subject. A bioactive agent can also have diagnostic properties. The bioactive agents include, but are not limited to, small molecules, nucleotides, oligonucleotides, polynucleotides, amino acids, oligopeptides, polypeptides, and proteins. Bioactive agents include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, codrugs, metabolites, analogs, homologues, congeners, derivatives, salts and combinations thereof. One skilled in the art will recognize that some of the groups, subgroups, and individual bioactive agents may not be used in some embodiments of the present invention.

Antiproliferatives can include, for example, actinomycin D, actinomycin IV, actinomycin I1, actinomycin X1, actinomycin C1, and dactinomycin (Cosmegen®, Merck & Co., Inc.). Antineoplastics or antimitotics include, for example, paclitaxel (Taxol®, Bristol-Myers Squibb Co.), docetaxel (Taxotere®, Aventis S.A.), methotrexate, azathioprine, vincristine, vinblastine, fluorouracil, doxorubicin hydrochloride (Adriamycin®, Pfizer, Inc.) and mitomycin (Mutamycin®, Bristol-Myers Squibb Co.), and any prodrugs, codrugs, metabolites, analogs, homologues, congeners, derivatives, salts and combinations thereof. Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors (Angiomax®, Biogen, Inc.), and any prodrugs, codrugs, metabolites, analogs, homologues, congeners, derivatives, salts and combinations thereof. Cytostatic or antiproliferative agents include, for example, angiopeptin, angiotensin converting enzyme inhibitors such as captopril (Capoten® and Capozide®, Bristol-Myers Squibb Co.), cilazapril or lisinopril (Prinivil® and Prinzide®, Merck & Co., Inc.); calcium channel blockers such as nifedipine; colchicines; fibroblast growth factor (FGF) antagonists, fish oil (omega 3-fatty acid); histamine antagonists; lovastatin (Mevacor®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, codrugs, metabolites, analogs, homologues, congeners, derivatives, salts and combinations thereof. Antiallergic agents include, but are not limited to, pemirolast potassium (Alamast®, Santen, Inc.), and any prodrugs, codrugs, metabolites, analogs, homologues, congeners, derivatives, salts and The amount of agent administered can vary according to factors such as type of disease, age, sex, and weight of the subject. Dosage regimens may be adjusted to optimize a therapeutic response. In some embodiments, a single bolus may be administered; several divided doses may be administered over time; the dose may be proportionally reduced or increased; or any combination thereof, as indicated by the exigencies of the therapeutic situation and factors known one of skill in the art. It is to be noted that dosage values may vary with the severity of the condition to be alleviated. Dosage regimens may be adjusted over time according to the individual need and the professional judgment of the person administering or supervising the administration of The agents, and the dosage ranges set forth herein are exemplary only and do not limit the dosage ranges that may be selected by medical practitioners.

An "effective amount" of an agent can be used to describe a therapeutically effective amount or a prophylactically effective amount. An effective amount can also be an amount that ameliorates the symptoms of a disease. A "therapeutically effective amount" refers to an amount that is effective at the dosages and periods of time necessary to achieve a desired therapeutic result and may also refer to an amount of active compound, prodrug or pharmaceutical agent that elicits any biological or medicinal response in a tissue, system, or subject that is sought by a researcher, veterinarian, medical doctor or other clinician that may be part of a treatment plan leading to a desired effect. A "prophylactically effective amount" refers to an amount that is effective at the dosages and periods of time necessary to achieve a desired prophylactic result. Typically, a prophylactic dose is used in a subject prior to the onset of a disease, or at an early stage of the onset of a disease, to prevent or inhibit onset of the disease or symptoms of the disease. A prophylactically effective amount may be less than, greater than, or equal to a therapeutically effective amount.

In some embodiments, an effective amount may result in amelioration of one or more symptoms of a disorder, prevention of the advancement of a disorder, or regression of a disorder. In one example, an effective amount preferably refers to the amount of a therapeutic agent that provides a measurable response of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of a desired action of the composition.

In some embodiments, an effective amount of an agent may range in concentration from about 0.001 nM to about 0.10 M; from about 0.001 nM to about 0.5 M; from about 0.01 nM to about 150 μM; from about 0.01 nM to about 500 μM; from about 0.01 nM to about 1000 μM, or any range therein. In some embodiments, an agent may be administered in an amount ranging from about 0.001 mg/kg to about 500 mg/kg; from about 0.005 mg/kg to about 400 mg/kg; from about 0.01 mg/kg to about 300 mg/kg; from about 0.01 mg/kg to about 250 mg/kg; from about 0.1 mg/kg to about 200 mg/kg; from about 0.2 mg/kg to about 150 mg/kg; from about 0.4 mg/kg to about 120 mg/kg; from about 0.15 mg/kg to about 100 mg/kg, from about 0.15 mg/kg to about 50 mg/kg, from about 0.5 mg/kg to about 10 mg/kg, or any range therein, wherein a human subject is assumed to average about 70 kg. A person of skill in the art will be able to routinely determine an effective amount for a given disease knowing a variety of subjective factors used by those of skill in determining the effective amount.

In some embodiments, an effective amount of an agent may be administered in an amount ranging from about 0.001 mg/kg to about 500 mg/kg; from about 0.005 mg/kg to about 400 mg/kg; from about 0.01 mg/kg to about 300 mg/kg; from about 0.01 mg/kg to about 250 mg/kg; from about 0.1 mg/kg to about 200 mg/kg; from about 0.2 mg/kg to about 150 mg/kg; from about 0.4 mg/kg to about 120 mg/kg; from about 0.15 mg/kg to about 100 mg/kg, from about 0.25 mg/kg to about 75 mg/kg, from about 0.5 mg/kg to about 50 mg/kg or any range therein.

The agents are administered using techniques known to one of skill to be compatible with an intended route of administration. Examples of routes of administration include, but are not limited to, parenteral such as, for example, intravenous, intradermal, intramuscular, and subcutaneous injection; oral; inhalation; intranasal; transdermal; transmucosal; and rectal administration.

The terms "administration" or "administering" refer to a method of incorporating a composition into the cells or tissues of a subject, either in vivo or ex vivo to diagnose, prevent, treat, or ameliorate a symptom of a disease. In one example, an agent can be administered to a subject in vivo parenterally. In another example, an agent can be administered to a subject by combining the compound with cell tissue from the subject ex vivo for purposes that include, but are not limited to, assays for determining utility and efficacy of a composition. In some embodiments, the administration can include a solubilizing agent and a local anesthetic such as lignocaine to ease discomfort at the site of injection.

The agents can be administered in dosage units. The term "dosage unit" refers to discrete, predetermined quantities of an agent that can be administered as unitary dosages to a subject. A predetermined quantity of active compound can be selected to produce a desired therapeutic effect and can be administered with a pharmaceutically acceptable carrier. The predetermined quantity in each unit dosage can depend on factors that include, but are not limited to, (a) the unique characteristics of the active compound and the particular therapeutic effect to be achieved, and (b) the limitations inherent in the art of creating and administering such dosage units.

The agents can be administered as a pharmaceutically acceptable formulation, wherein an agent is delivered in a pharmaceutically acceptable carrier to a subject. A "pharmaceutically acceptable carrier" is any diluent, adjuvant, excipient, or vehicle with which a composition is administered that is known to one of skill, as well as approved and listed by a state or federal regulatory agency, the U.S. Pharmacopeial Convention, or other generally recognized sources. The pharmaceutical carriers include any and all physiologically compatible solvents, dispersion media, coatings, antibacterial and antifungal agents, isotonic and absorption delaying agents, and the like. Examples of pharmaceutical carriers include, but are not limited to, sterile liquids, such as water, oils and lipids such as, for example, phospholipids and glycolipids. These sterile liquids include, but are not limited to, those derived from petroleum, animal, vegetable or synthetic origin such as, for example, peanut oil, soybean oil, mineral oil, sesame oil, and the like. Water can be a preferred carrier for intravenous administration. Saline solutions, aqueous dextrose and glycerol solutions can also be liquid carriers, particularly for injectable solutions.

Suitable pharmaceutical excipients include, but are not limited to, starch, sugars, inert polymers, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain minor amounts of wetting agents, emulsifying agents, pH buffering agents, or a combination thereof. The agents can take the form of solutions, suspensions, emulsion, tablets, pills, capsules, powders, sustained-release formulations and the like. Oral formulations can include standard carriers such as, for example, pharmaceutical grades mannitol, lactose, starch, magnesium stearate, sodium saccharine, cellulose, magnesium carbonate, and the like. See Martin, E. W. Remington's Pharmaceutical Sciences. Supplementary active compounds can also be incorporated into The agents.

Pharmaceutical formulations for parenteral administration may include liposomes and emulsions. Liposomes and emulsions are delivery vehicles or carriers that are especially useful for hydrophobic drugs. Furthermore, one may administer the drug in a targeted drug delivery system such as, for example, in a liposome coated with target-specific antibody. The liposomes will bind to the target protein and be taken up selectively by the cell expressing the target protein.

The compounds may be administered as suspensions such as, for example, oily suspensions for injection. Lipophilic solvents or vehicles include, but are not limited to, fatty oils such as, for example, sesame oil; synthetic fatty acid esters, such as ethyl oleate or triglycerides; and liposomes. Suspensions that can be used for injection may also contain substances that increase the viscosity of the suspension such as, for example, sodium carboxymethyl cellulose, sorbitol, or dextran. Optionally, a suspension may contain stabilizers or agents that increase the solubility of the compounds and allow for preparation of highly concentrated solutions.

In one embodiment, an injectable solution can be prepared by incorporating an effective amount of an active compound in a solvent with any one or any combination of desired additional ingredients described above, filtering, and then sterilizing the solution. In another embodiment, dispersions can be prepared by incorporating an active compound into a sterile vehicle containing a dispersion medium and any one or any combination of desired additional ingredients described above. Sterile powders can be prepared for use in sterile and injectable solutions by vacuum drying, freeze-drying, or a combination thereof, to yield a powder that can be comprised of the active ingredient and any desired additional ingredients. Moreover, the additional ingredients can be from a separately prepared sterile and filtered solution. In another embodiment, the extract may be prepared in combination with one or more additional compounds that enhance the solubility of the extract.

In some embodiments, the compounds can be administered by inhalation through an aerosol spray or a nebulizer that may include a suitable propellant such as, for example, dichlorodifluoromethane, trichlorofluoromethane, dichlorotetrafluoroethane, carbon dioxide, or a combination thereof. In one example, a dosage unit for a pressurized aerosol may be delivered through a metering valve. In another embodiment, capsules and cartridges of gelatin, for example, may be used in an inhaler and can be formulated to contain a powderized mix of the compound with a suitable powder base such as, for example, starch or lactose.

The agents can be administered as a pharmaceutical formulation by injection. In some embodiments, the formulation can comprise an agent in combination with an aqueous injectable excipient. Examples of suitable aqueous injectable excipients are well known to persons of ordinary skill in the art, and they, and the methods of formulating the formulations, may be found in such standard references as Alfonso AR: Remington's Pharmaceutical Sciences, 17th ed., Mack Publishing Company, Easton Pa., 1985. Suitable aqueous injectable excipients include water, aqueous saline solution, aqueous dextrose solution, and the like, optionally containing dissolution enhancers for the acid-modified arabinogalactan protein composition, such as 3 10% mannitol or other sugars, 3 10% glycine or other amino acids. An agent can be injected subcutaneously, intramuscularly, intraperitoneally, or intravenously. In some embodiments, intravenous administration is used, and it can be continuous intravenous infusion over a period of a few minutes to an hour or more, such as around fifteen minutes. The amount administered may vary widely depending on the type of formulation, size of a unit dosage, kind of excipients, and other factors well known to those of ordinary skill in the art. The formulation may comprise, for example, from about 0.001% to about 10% (w/w), from about 0.01% to about 1%, from about 0.1% to about 0.8%, or any range therein, with the remainder comprising the excipient or excipients.

The agents can be administered in combination with one or more additional active agents. In some embodiments, the agent can be administered in conjunction with at least one other therapeutic agent for the disease state being treated, such as the administration of a chemotherapeutic agent with an agent capable of stimulating hematopoiesis such as, for example, erythropoietin, thrombopoietin, granulocyte colony stimulating factor (G-CSF), IL-3, and the like.

In some embodiments, at least one of the agents is selected from the group consisting of antiproliferatives, antineoplastics, antimitotics, anti-inflammatories, antiplatelets, anticoagulants, antifibrins, antithrombins, antibiotics, antiallergics, antioxidants, and any prodrugs, codrugs, metabolites, analogs, homologues, congeners, derivatives, salts and combinations thereof.

In some embodiments, at least one of the agents includes an effective amount of a hematopoietic agent including, but not limited to, granulocyte colony stimulating factor (G-CSF), granulocyte macrophage colony stimulating factor (GM-CSF), erythropoietin and erythropoiesis stimulating protein, thrombopoietin, interleukin-3, and derivatives thereof. Examples of G-CSF include, but are not limited to, filgrastim (NEUPOGEN), and derivatives thereof, such as PEG-FILGRASTIM. An example of GM-CSF includes sagramostim (LEUKINE). An example of erythropoietin is epoetin alfa (EPREX). An example of erythropoiesis stimulating protein is darbepoetin alfa (NESP, ARANESP). The hematopoietic agent can be administered, for example, for 30 minutes, 1 hour, 2 hours, 4 hours, 8 hours, 12 hours, 18 hours, 1 day, 2 days, 3 days, 4 days, 5 days, 6 days, 7 days, 8 days, 9 days, 10 days, 2 weeks, 3 weeks, 4 weeks, 6 weeks, 3 months, 6 months, 1 year, or any amount of time considered necessary by one of skill. The G-CSF can be NEUPOGEN, for example, administered in an amount ranging from about 0.1 µg/kg to about 1 mg/kg, from about 0.5 µg/kg to about 500 µg/kg, from about 1 µg/kg to about 250 µg/kg, from about 1 µg/kg to about 100 µg/kg from about 1 µg/kg to about 50 µg/kg, or any range therein.

In some embodiments, at least one of the agents is a nucleic acid construct, which is an artificially constructed nucleic acid sequence that can be introduced to a target tissue or cells by way of, for example, a vector. The vector can include, but is not limited to, a plasmid, a cosmid, or a virus. The constructs can include at least one polynucleotide that encodes for a desired protein, wherein the polynucleotide is operably connected to a regulatory sequence. An "operably connected" polynucleotide and regulatory sequence is a functionally linked structure, wherein the regulatory sequence directs the transcription of the nucleic acid. A promoter or enhancer is operably linked to a coding sequence if it affects the transcription of the coding sequence. An example of such a construct is Ad-LIGHT$^m$, a recombinant adenovirus that operably links the DNA that encodes for a mutant form of LIGHT, a tumor necrosis factor (TNF) that interacts with lymphotoxin β receptors and herpes virus entry mediators that are mainly expressed on stromal cells and T-cells. The construct of Ad-LIGHT$^m$ is discussed in International Publ. No. WO 2008/098183 and U.S. Patent Publ. No. 20050025754, each of which is hereby incorporated herein by reference in its entirety. The Ad-LIGHT$^m$ can be administered alone or in combination with another agent, including radiation, an immunotherapeutic agent, a chemotherapeutic agent, and antibody, and the like, for example.

In some embodiments, a construct may be administered in an amount effective to prevent further proliferation of tumor cells and/or to cause regression of the tumor, without being overly toxic to the cell or the subject receiving the treatment. In some embodiments, the construct may be delivered to the subject in about 6 doses over a period ranging from about 7 days to about 21 days, from about 7 days to about 70 days, from about 7 days to about 45 days, or any range therein. In some embodiments, from about 3 doses to about 6 doses can be administered each week for a period of time ranging from about 21 days to about 42 days, from about 18 days to about 60 days, from about 28 days to about 49 days, or any range therein. An example of an effective amount of Ad-LIGHT$^m$ can be, for example, about $1 \times 10^9$ PFU delivered intratumorally, where the viral particle-to-PFU ratio is 10:1. In some embodiments, the effective amount of Ad-LIGHT$^m$ can range from about $1 \times 10^7$ PFU to about from $1 \times 10^{11}$ PFU, from about $1 \times 10^8$ PFU to about from $1 \times 10^{10}$ PFU, from about $5 \times 10^8$ PFU to about from $5 \times 10^{10}$ PFU, or any range therein.

The combinations of agents can be administered concomitantly, sequentially, or cyclically to a subject. Cycling therapy involves the administering a first agent for a predetermined period of time, administering a second agent for a second predetermined period of time, and repeating this cycling for any desired purpose such as, for example, to enhance the efficacy of the treatment. In some embodiments, the agents can be administered at points in time that vary by about 15 minutes, 30 minutes, 1 hour, 2 hours, 4 hours, 8 hours, 12 hours, 18 hours, 24 hours, 48 hours, or 1 week in time, or any combination of such points in time.

The agents can also be administered concurrently. The term "concurrently" is not limited to the administration of agents at exactly the same time, but rather means that the agents can be administered in a sequence and time interval such that the agents can work together to provide additional benefit. Each agent can be administered separately or together in any appropriate form using any appropriate means of administering the agent or agents.

Without intending to be limited to any theory or mechanism of action, the following examples are provided to further illustrate the teachings presented herein. It should be appreciated that there are several variations contemplated within the skill in the art, and that the examples are not intended to be construed as providing limitations to the claims.

Example 1

This example provides the materials and methods used throughout the remainder of the examples.

Mice, Cell Lines and Reagents:

C57BL/6, Nude, B6/Rag, and Balb/c mice were purchased from Jackson Laboratory at 6-7 weeks old. 2C TCR-transgenic mice were bred and maintained in the specific pathogen free (SPF) facility at the University of Chicago. For all experiments, mice were between the ages of 6-16 weeks of age, bred under SPF conditions and used in accordance to the animal experimental guidelines set by the Institute of Animal Care and Use Committee (IACUC).

The B16-SIY melanoma cells were generated as described in C. Blank et al., *Cancer Res* 64, 1140 (Feb. 1, 2004), incorporated herein by reference in its entirety. B16, B16-SIY were grown in RPMI 1640 (Invitrogen Life technologies) supplemented with 10% FCS (Gemini).

The 4T1 cells are a 6-thioguanine-resistant cell line derived from spontaneous mammary carcinoma as described by F. R. Miller, B. E. Miller, G. H. Heppner, *Invasion Metastasis* 3, 22 (1983), incorporated herein by reference in its entirety. The 4T1 tumor cells were grown in Dulbecco's Modified Eagle's Medium (DMEM, Invitrogen Life Technologies) supplemented with 10% FCS.

Monoclonal antibodies produced by hybridomas were purified from the culture supernatant with protein G column using standard procedures. Systemic depletion was confirmed by peripheral blood fluorescence-activated cell sorting (FACS) staining. A depleted $CD8^+$ subset represented <0.5% of the total lymphocytes while other subsets were normal. Anti-2C TCR (1B2) antibody was obtained from T. Gajeweski of The University of Chicago. The 1B2 antibody was conjugated to FITC or biOT-1n by the Monoclonal Antibody Facility of The University of Chicago. All other antibodies for FACS were purchased from BD Biosciences.

The generation of Ad-LIGHT<sup>m</sup> (recombinant adenoviral vectors expressing the murine LIGHT gene) is described in P. Yu et al., *J Immunol* 179, 1960 (Aug. 1, 2007), incorporated herein by reference in its entirety. International Patent Application No. PCT/US2008/053448 is also hereby incorporated herein in its entirety by reference.

Generation of Bone Marrow Derived Dendritic Cells (BMDC) and Mouse Lymphoid Dendritic Cells (DC):

For DC harvest for FACS, draining lymph node tissue (DLN) and spleen tissue (SP) were digested with 1.5 mg/ml collagenase and 100 μg/ml DNase for 20 min at 37° C. and then gently pipetted in the presence of 0.01 M EDTA for 1 min. Single-cell suspensions were stained and analyzed by flow cytometry on a FACSCanto (BD Biosciences). For BMDC, bone marrow (BM) cells from femurs of C57BL/6 were cultured in RPMI 1640 (Invitrogen Life Technologies) supplemented with 10% flow cytometry standard (FCS, HyClone) and recombinant mouse granulocyte-macrophage colony-stimulating factor (GM-CSF, R&D Systems) as described in M. B. Lutz et al., *J Immunol Methods* 223, 77 (Feb. 1, 1999), incorporated herein by reference in its entirety.

Adoptive Transfer of T-Cells:

Lymph node (LN) cells and splenocytes (SP) were isolated from 2C TCR Tg mice. A total of $2\times10^6$ 2C cells were labeled with carboxyfluorescein succinimidyl ester (CFSE) and then adoptively transferred (i.v.) into B16-SIY tumor bearing C57BL/6 mice as described in P. Yu et al., *J Immunol* 179, 1960 (Aug. 1, 2007) and P. Yu et al., *Nat Immunol* (Jan. 4, 2004), each of which is incorporated herein by reference in its entirety. Cells were isolated from the inguinal LNs (DLNs), SP, or tumors at the time indicated. CFSE dilution was evaluated as described in Yu, at Id.

TCR Tetramer and FACS Staining:

For tetramer staining, tumor, DLN, and SP were excised from the mouse, chopped, and collagenase digested (1.5 mg/ml) for 20 min in a shaking incubator at 37° C. Single cell suspensions of cells were incubated with 2.4G2 to block antibody binding to the Fc receptors, $CD11c^+$-APC, 1 μg $SIY-K^b$-specific m67 TCR tetramer-PE, and mAb $CD11b^+$-PerCP-Cy5.5.

Samples were analyzed on a FACSCanto (BD Biosciences), and data were analyzed with FlowJo software (TreeStar, Inc.). The m67 ab was a generous gift from David Kranz of The University of Illinois and Hans Schreiber of The University of Chicago.

Local Tumor Irradiation and Systemic Chemotherapy:

The mice were irradiated using an x-ray generator (PCM 1000; Pantak) at the doses indicated by each experiment. Each mouse was protected with a lead cover with only tumor exposed, allowing local irradiation. For systemic chemotherapy, tumor-bearing mice were injected i.p. with 20 mg/kg paclitaxel (Ameristat Pharmaceuticals) for 4T1 bearing mice and 200 mg/kg dacarbazine (Bedford Laboratories) for B16 bearing mice.

Tumor Injection, Treatments, and Evaluation of Metastases Using a Colonogenic Assay:

Cultured cancer cells were trypsinized, washed with media, and injected s.c. on the back. Tumor size was determined at 3-4 day intervals. Tumor volumes were measured along three orthogonal axes (a, b, and c) and calculated as tumor volume=abc/2.

For surgical excision of primary 4T1 and B16-CCR7 tumors, mice were anesthetized, and tumors were resected with sterilized instruments. A colonogenic assay was used to evaluate metastases in 4T1 and B16-CCR7 tumors as described in B. A. Pulaski, S. Ostrand-Rosenberg, *Curr Protoc Immunol* Chapter 20, Unit 20 2 (May, 2001), incorporated herein by reference in its entirety. Lungs for 4T1 tumor or DLN for B16-CCR7 were collected, chopped and dissociated in DMEM supplemented with 10% FCS containing 1.5 mg/ml collagenase type D (Sigma-Aldrich) for 20 min in 37° C. shaking incubator. Single cell suspensions were plated at various dilutions in media supplemented with 10% FCS and selection drug. 4T1 is resistant to 6-thioguanine (60 mM) and B16-CCR7 is resistant to G418 (0.7 mg/ml). Individual colonies representing micrometastases were counted after 5-10 days.

The administration of therapies include inoculating tumor nodules with an indicated amount of therapeutic such as, for example, Ad-LIGHT<sup>m</sup> or Ad-control virus, intratumorally.

Statistical Analyses:

Statistics were done using an unpaired student two-tailed t test, and error bars represent standard deviations. For survival curves, statistics were done using the logrank (Mantel-Cox) test.

Example 2

The Resistance of Poorly-Immunogenic Cells to Radiation Therapy is Overcome in a T-Cell Dependent Fashion This example shows at least that (1) radiation induces an immune response that can eradicate a tumor or reduce the size of the tumor; (2) the resistance of poorly-immunogenic cells to radiation can be overcome by stimulating T-cell activity; and (3) immunodeficiency or immunosuppression can inhibit or abrogate the anti-tumor effects of radiation therapy. Since current immunodeficient xenograft models could not have provided these results, one of skill will appreciate the need for an immunocompetent xenograft model in view of these results.

FIGS. 1A through 1D show that immune-deficient mice having a poorly immunogenic tumor are more resistant to radiation therapy than immunocompetent mice, according to some embodiments. Note that "*" indicates a significant p-value, "" indicates a very significant p-value, and "*" indicates an extremely significant p-value.

Wild-type (WT) C57BL/6 and nude mice (n=10) were injected with $2\times10^6$ B16 melanoma cells, a cell line that is well established to a highly aggressive, poorly immunogenic, radio-resistant cancer. The cancer was treated 7 d later with a modified, hypofractionated radiation therapy (HFRT), which in this example was one high single 20 Gy dose of radiation applied locally. Results are compared to WT and nude "control" mice that were injected with the cancer cells but not treated with the radiation. FIG. 1A shows that the mice treated with radiation show significant regression and have significant smaller tumor size (**p=0.002 at day 10 post RT), as well as an increase of infiltrating T-cells at about 1 week to about 2 weeks after radiation treatment (not shown). Nude mice were used to assess the contribution of the T-cells and, impressively, the tumor in the nude mice remained resistant to the radiation therapy. Similar results were seen using B- and T-cell deficient B6/Rag−/− mice (not shown). As such, these findings show that the resistance of poorly-immunogenic cells to radiation therapy, such as the B16 cells, can be overcome in a T-cell dependent fashion. The time "after radiation treatment" refers to the time passing after the first dosage of radiation treatment is administered, e.g., "10 days post RT" refers to 10 days after the first administration of radiation. In some embodiments, the radiation treatment is administered in a single dose. In some embodiments, the radiation treatment is administered in fractionated doses. Any time frame known to one of skill can be used, such as minutes, hours, days, weeks, or months, for example.

To assess the contribution of the immunogenicity of the tumor to the results, a Kb-binding peptide, SIYRYYGL (SIY), was introduced to the B16 cells to produce B16-SIY, a tumor having a strong antigen. The WT mice (n=9-10) or nude mice (n=8-12) were injected with $2\times10^5$ B16-SIY and treated 10 days later with one high single 25 Gy dose of radiation. Generally speaking, the mice treated with radiation show showed significant smaller tumor size (***p=0.0002 on day 12 post RT). FIG. 1B shows that radiation therapy alone was sufficient to completely reject the B16-SIY tumors in 9/10 mice, effectively "curing" the mice. In nude mice, on the other hand, the tumors continued to grow progressively and killed 9/9 of the host mice. As such, these findings again show that the resistance of poorly-immunogenic cells to radiation therapy, such as the B16 cells, can be overcome in a T-cell dependent fashion.

The contribution of CD8+ killer cells on the effectiveness of radiation therapy was tested. WT mice were injected with $1\times10^5$ B16, and the tumors were allowed to establish for 14 days. The WT mice having established B16 tumors were treated with HFRT on day 14, where 15 Gy/day of radiation was given for three days, on each of days 0, 1, and 2, following the start of radiation therapy (these were days 14, 15, and 16 following tumor inoculation). The radiation was given in conjunction with a treatment that depleted CD8+ cells. The treatment that depleted CD8+ cells was the administration of CD8 antibodies, αCD8, in an amount of 200 μg/mouse (n=5-9/group) on each of days 0, 4, and 8 following the start of radiation therapy (these were days 14, 18, and 22 following tumor inoculation).

FIG. 1C shows the tumor growth curve and FIG. 1D shows the percent survival of the WT mice. FIG. 1C shows that when radiation therapy is accompanied by a depletion of CD8 cells in the WT mice, the size of tumor increased significantly when compared to radiation therapy in the presence of CD8 cells (p=0.0073 at d14). FIG. 1D shows that survival increases after radiation therapy in the presence of CD8 cells (*p=0.0001) but survival decreases after radiation therapy when the radiation therapy is accompanied by a depletion of CD8 cells (***p=0.0009. *p<0.05, p<0.01, *p<0.001). Similar experiments were repeated 3 times for FIGS. 1A through 1D. As such, these findings again show that the resistance of poorly-immunogenic cells to radiation therapy, such as the B16 cells, can be overcome in a T-cell dependent fashion.

Example 3

Radiation Therapy Stimulates Immune Response by Activating Tumor-Specific T-Cells Without intending to be bound by any theory or mechanism of action, this example shows that radiation therapy promotes activation of dendritic cells (DC) and migration of dendritic cells (DC) to the draining lymph nodes (DLN). Since current immunodeficient xenograft models could not have provided these results, one of skill will appreciate the need for an immunocompetent xenograft model in view of these results.

To show whether radiation therapy re-energizes the priming of naïve T-cells, naïve CD8+ 2C transgenic T-cells were CFSE labeled and then adoptively transferred into B16-SIY tumor-bearing mice. The naïve CD8+ 2C transgenic T-cells are antibody specific and were selected for their ability to recognize the SIY antigen through both direct and indirect presentation.

Figure 2:
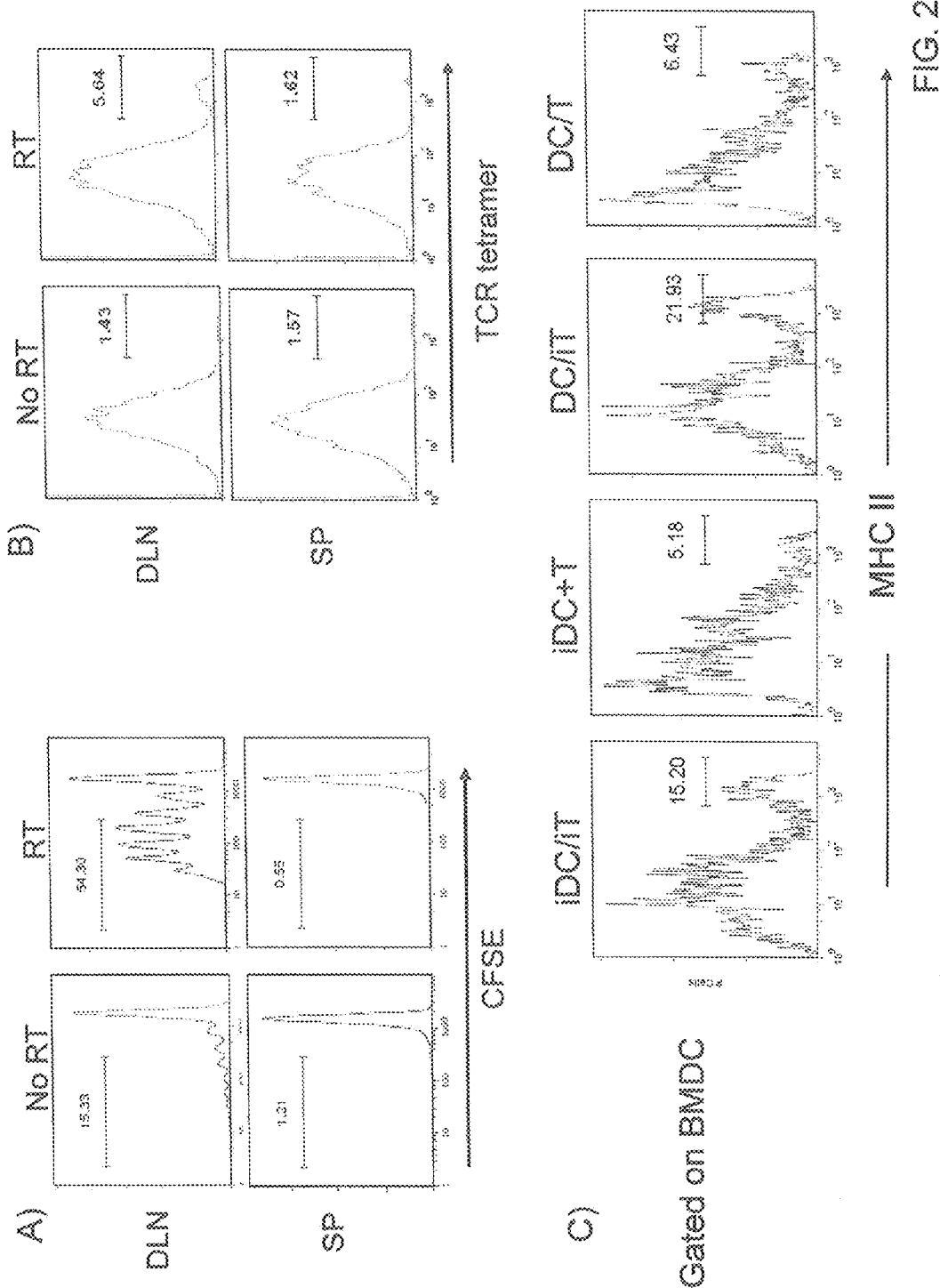
FIGS. 2A through 2C show that radiation therapy stimulates immune response by activating tumor-specific T-cells, according to some embodiments.

FIGS. 2A through 2C show that radiation therapy stimulates immune response by activating tumor-specific T-cells, according to some embodiments. In this procedure, $5\times10^5$ B16-SIY tumor cells were injected s.c. into the lower back of C57BL/6 mice, and the tumors were allowed 14 days to establish. After the establishment period, the mice received 20 Gy of local radiation on the tumors, and CFSE labeled naïve CD8+ 2C transgenic T-cells were adoptively transferred i.v. to the mice. The mice were sacrificed for analysis of the DLN and spleen (SP) tissue 96 hours after the adoptive transfer of the naïve T-cells. The degree of CFSE dilution via FACS was determined by gating on $1B2^+CD8^+$ lymphocyte population. The results are compared to "control" mice that did not receive the localized administration of 20 Gy radiation on the tumors.

FIG. 2A shows that the mice receiving radiation therapy have more proliferative T cells than the control mice that did not receive radiation therapy (p=0.01). In fact, the antibody-specific naïve T-cells exhibited robust priming in the DLNs after radiation therapy and, in contrast, nominal proliferation in the control mice. Accordingly, radiation therapy promotes priming of antibody-specific cells.

To identify a cause for the increased priming, as above, $5 \times 10^5$ B16-SIY tumor cells were injected s.c. into the lower back of C57BL/6 mice, and the tumors were allowed 14 days to establish. After the establishment period, the mice received 20 Gy of local radiation on the tumors, and the mice were sacrificed 5 days later. Tissue from the tumor, DLN, and SP was harvested, collagenase digested, and stained for FACS with a TCR tetramer to identify APCs expressing SYI peptide. The TCR tetramer binds to SYI peptide presented by MHC class I molecules and provides a measure, in this example, of whether SIY+DCs are increased in the tumor or the DLNs after radiation therapy. The cells were gated on $CD11c^+$ cells. Similar experiments were repeated 2 times, and the mice receiving radiation therapy shows more positive cells than the group not receiving radiation therapy (p<0.05).

FIG. 2B shows that there was an increase in SIY peptide-presenting CD11c+ cells in the DLN, according to some embodiments. In contrast, these results did not show in the SP. Increased CD11c+TCR tetramer+cells were found inside the tumors after radiation therapy (data not shown), showing that DCs activate and migrate to the DLN. Accordingly, radiation therapy promotes activation of DCs in DLNs and migration of DCs from tumors to DLNs for better priming of T-cells.

To show whether radiation therapy causes maturation of DCs, irradiated bone marrow derived dendritic cells (BM-DCs) (iDC) and non-irradiated BMDCs (DC) were co-cultured with irradiated B16 tumor cells (iT) and non-irradiated B16 tumor cells (T) for 48 hours. The BMDC cells received 5 Gy radiation therapy or no radiation therapy and the B16 tumor received 60 Gy radiation therapy. The cells were harvested after the 48 hours, stained for FACS, and tested for maturation markers on the BMDCs.

FIG. 2C shows that coharvesting an irradiated tumor cell with either an irradiated DC or non-irradiated DC results in upregulation of MHC class II molecule expression, whereas coharvesting a non-irradiated tumor-derived cell with either an irradiated or non-irradiated DC results in a lack of MHC class II expression. The Irradiated tumors induced DC maturation and have more class II positive cells than non irradiated groups (p<0.05). Accordingly, radiation therapy stimulates the tumor-derived cell and signals the DCs.

Example 4

Conventional Chemotherapy or Prolonged Radiation can Reduce or Eliminate Radiation-Activated Immunity and Anti-Tumor Effect This example shows that chemotherapy can act as an immunosuppressive by reducing or eliminating radiation-activated immunity and anti-tumor effect. Since current immunodeficient xenograft models could not have provided these results, one of skill will appreciate the need for an immunocompetent xenograft model in view of these results.

FIGS. 3A through 3D show that the use of a standard clinical combination of using chemotherapy as an adjuvant to a localized radiation therapy can significantly hinder tumor regression, according to some embodiments.

The effect of adding dacarbazine as an adjuvant to radiation therapy of melanoma cells was determined by injecting s.c. $2 \times 10^5$ B16-CCR7 cells into mice. Control mice receive the melanoma cells and no radiation, and other mice receive radiation therapy only, radiation therapy with depletion of CD8 cells using αCD8 antibodies, chemotherapy only, or a combination of radiation therapy followed by chemotherapy. The mice receiving radiation received a dose of 15 Gy on each of days 14, 15, and 16. On days 7 and 14 following radiation therapy, the mice receiving a combination of radiation therapy and chemotherapy received 200 mg/kg dacarbazine i.p.

Figure 3:
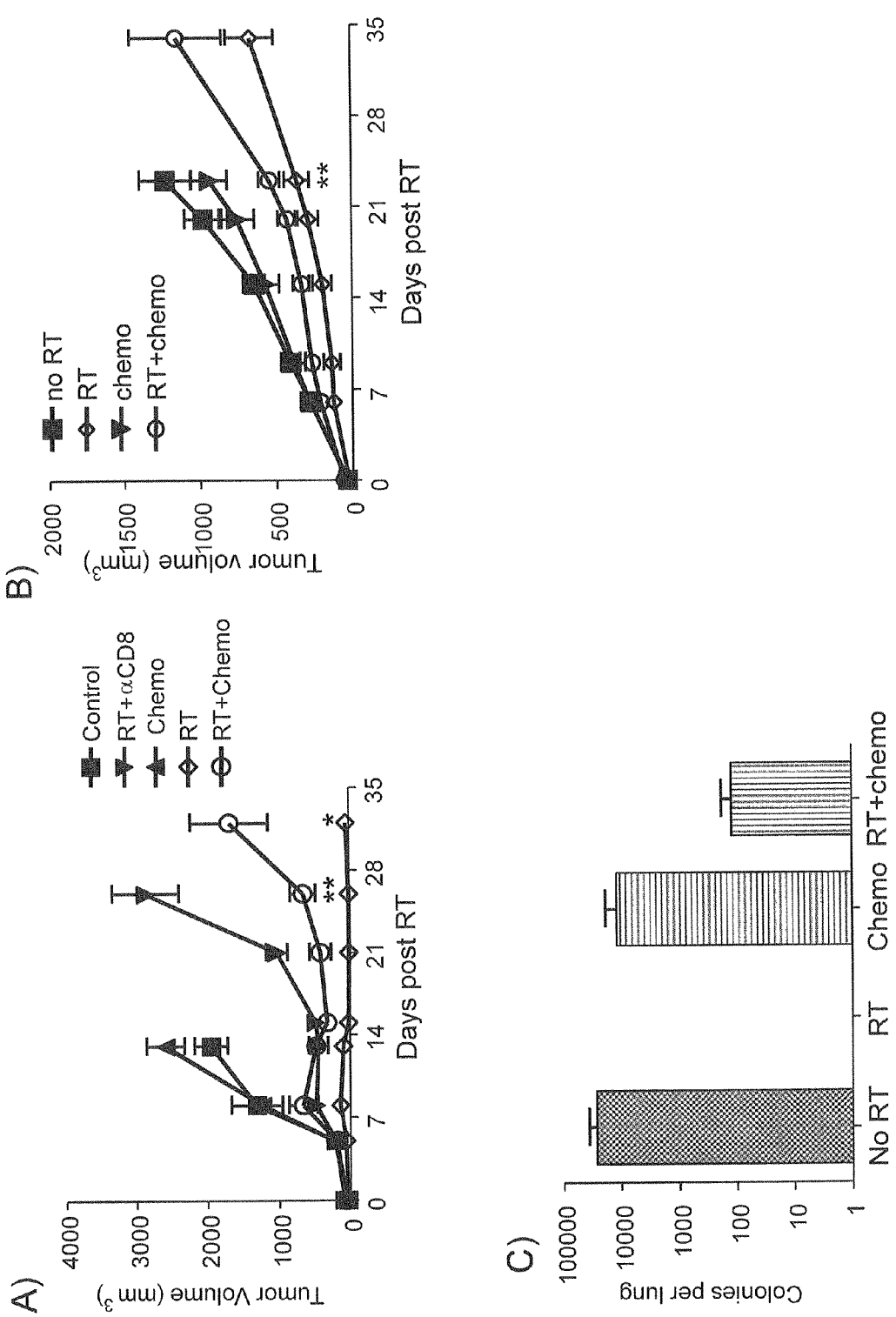
FIGS. 3A through 3E show that the use of a standard clinical combination of using chemotherapy as an adjuvant to a localized radiation therapy can significantly hinder tumor regression, according to some embodiments.
Figure 3:
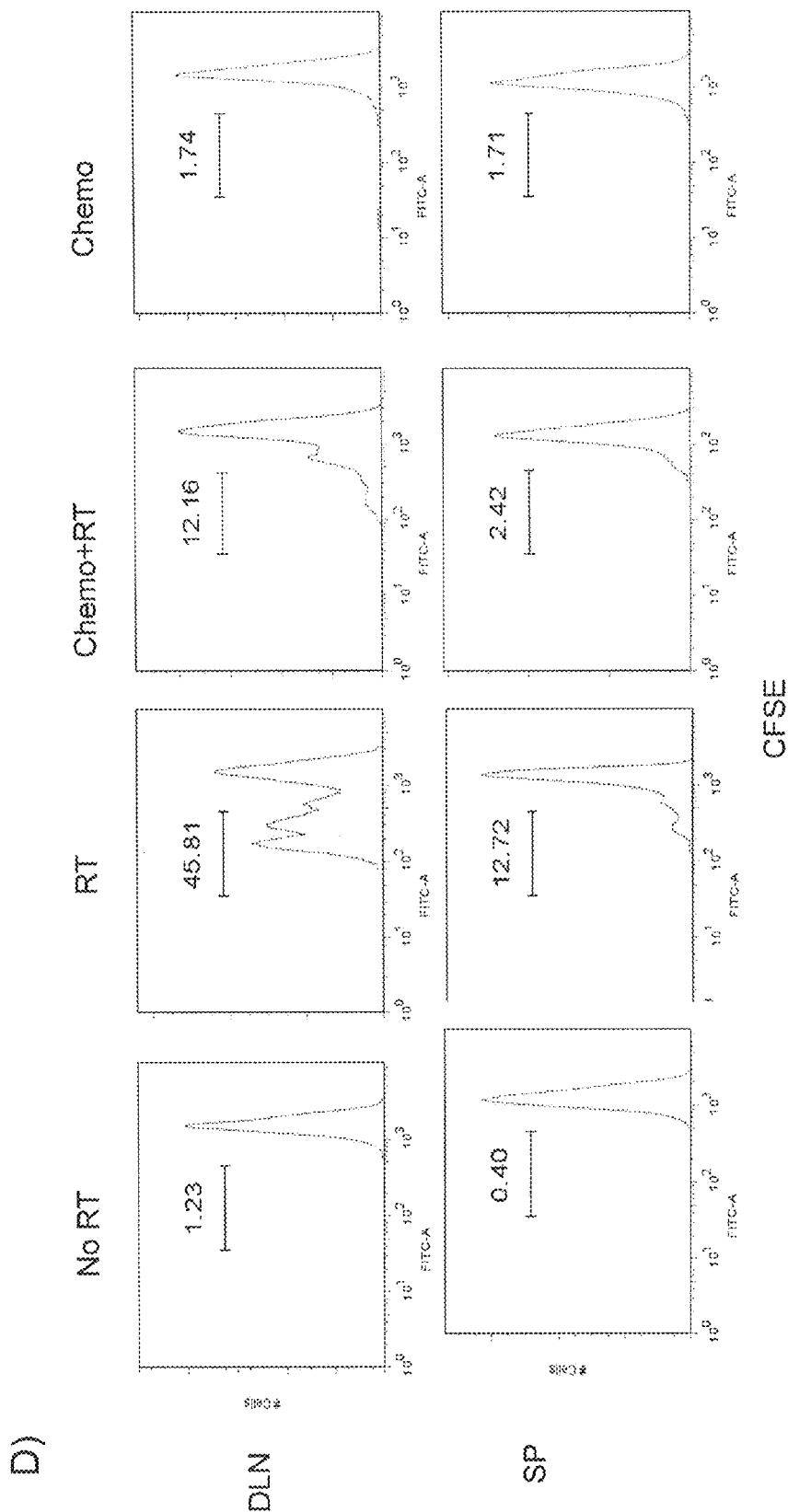
Figure 3:
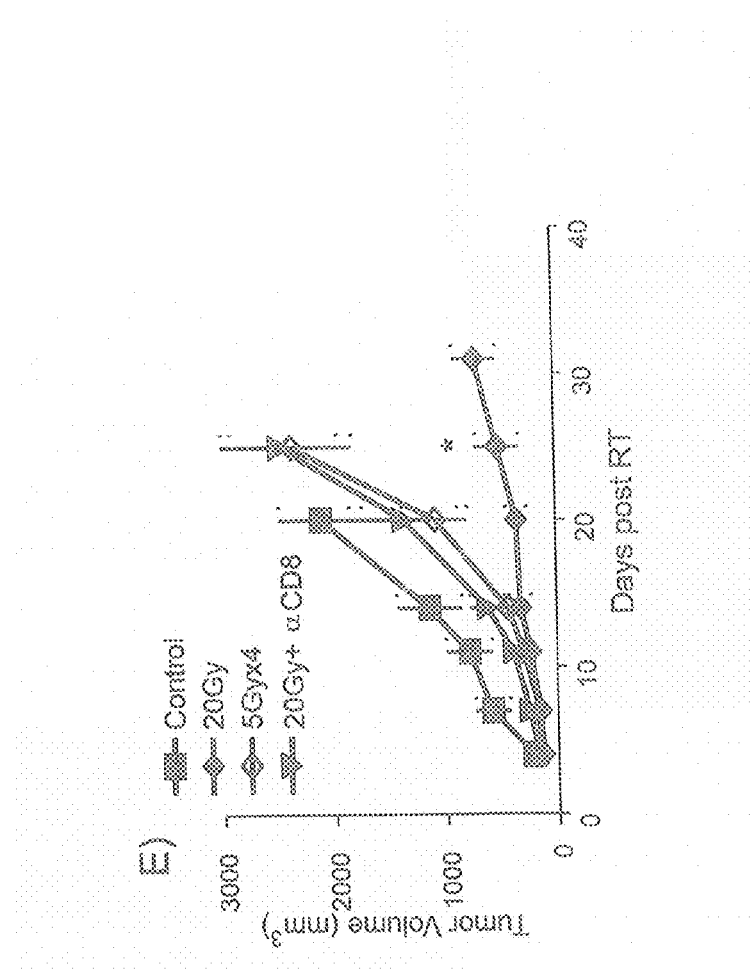

FIG. 3A shows that the addition of dacarbazine after radiation therapy significantly hindered melanoma tumor regression and promoted tumor outgrowth. The B6 mice receiving only the radiation therapy showed a significantly reduced tumor size at 13 days after radiation therapy (*p=0.0006). Addition of dacarbazine after radiation therapy led to significant regrowth of the tumor at day 26 after radiation therapy (p=0.0075), and at day 32 after radiation therapy (*p=0.015) (n=3-5). Radiation therapy in mice with depleted CD8 cells also seriously hindered tumor regression, and the use of dacarbazine alone appeared to show no tumor regression when compared to the control mice.

A 4T1 breast tumor model was used to show the results of the test on a different type of tumor. $1 \times 10^5$ 4T1 tumor cells were injected and allowed to establish for 14 days. Balb/c control mice receive the breast cancer cells and no radiation, and other mice receive radiation therapy only, chemotherapy only, or a combination of radiation therapy followed by chemotherapy. The mice receiving radiation received a dose of 15 Gy on each of days 14, 15, and 16. On days 7 and 14 following radiation therapy, the mice receiving a combination of radiation therapy and chemotherapy received 20 mg/kg paclitaxel i.p.

FIG. 3B shows that the addition of paclitaxel after radiation therapy significantly hindered melanoma tumor regression and promoted tumor outgrowth. The Balb/c mice receiving only the radiation therapy showed a significantly reduced tumor size at 23 days after radiation therapy (***p=0.008) (4-9 per group). The influence of chemotherapy on radiation therapy-mediated tumor regression was less pronounced with regard to the primary tumor.

The 4T1 breast tumor model was used in a metastases assay to show that lung metastases can be eradicated by radiation therapy to the primary tumor whereas the addition of chemotherapy can actually increase the number of tumor colonies by 100 fold. $1 \times 10^5$ 4T1 tumor cells were injected s.c. to the Balb/c mice, and the mice received 15 Gy of radiation on each days 12, 13, and 14. On days 7 and 14 following the radiation therapy, 20 mg/kg of paclitaxel was administered i.p. Control mice received the tumor cells but did not receive any therapies.

FIG. 3C shows that no colonies were detected in the lungs after radiation therapy alone. However, there was a 100 fold increase in tumor colonies in the lungs of Balb/c mice bearing the 4T1 tumor after adding chemotherapy (n=3-7). The chemotherapy alone had little effect on the degree of metastases in the lungs when compared to the control mice, which showed substantial metastases in the lungs.

In order to identify the effects of the chemotherapy on CD8+ T-cell priming, $5 \times 10^5$ B16-SIY melanoma cells were injected s.c. in the B6 mice. On day 17, $2 \times 10^6$ CFSE labeled naïve CD8+ 2C transgenic T-cells were adoptively transferred into the B16-SIY tumor bearing mice. The mice were treated locally with 20 Gy of radiation on day 0 following the transfer. 200 mg/kg dacarbazine i.p. was given two days after the adoptive transfer, and DLN and SP were harvested on day 21 to determine the CFSE dilution in the DLN and SP.

FIG. 3D shows that the addition of chemotherapy to the radiation therapy treated B6 mice bearing B16-SIY tumor can eliminate the priming of CD8+ T-cells. The administration of chemotherapy alone did not elicit proliferation of cytotoxic lymphocytes (CTL) when compared to the control mice. These results are shown in both the DLN and SP, but are more pronounced in the DLN.

Conventional fractionated radiation therapy delivers low doses of radiation over a course of about 3 to about 8 weeks. To test the potentially damaging effects these fractionated regimes may have on radiation initiated immune responses, the effects of the dosing regimes were determined by comparing single dosing of radiation to multiple dosing of radiation. $5 \times 10^6$ B16-SIY melanoma cells were injected s.c. to the B6 mice. Two protocols of radiation administration were used: one group of mice received radiation therapy in a single 20 Gy dose, and another group of mice received radiation therapy in a dose fractionation of 5 Gyx4 (5 Gray/day for 4 days over a two week period). Another group of mice received the single 20 Gy dose but also received CD8 depletion using αCD8 antibody, which was administered on day 0, 4, 8, and 12 after radiation therapy. The control mice only received the melanoma cells with no additional treatment.

FIG. 3E shows that repeated treatment of radiation results in significant regrowing of B16 tumor mass in B6 mice at day 25 (*p=0.03) (n=4-6). The administration of a single 20 Gy dose provided the best results. With the repeated treatment, the tumors relapsed in a manner analogous to the CD8-depleted group that received the 20 Gy radiation therapy in a single dose. The repeated "fractionated" dose appears to kill T-cells, or at least T-cell response, an effect that is not seen in a standard xenograft model and, thus, not appreciated by the medical community.

Results from B6 Rag-1 deficient mice showed similar aggressive growth of B16-SIY tumors when treated with either 20 Gy or 5 Gyx4. Wild-type B6 mice, on the other hand, showed either a delayed response in 100% of the cases (26/26 mice) or a cure in 35% of the cases (9/26 mice) at 20 Gy. Moreover, the wild-type mice showed poor therapeutic impact with 5 Gyx4 or 5 Gyx6 protocols with no cure (0/20 mice) (data not shown).

Accordingly, these findings suggest that the current standard fractionated radiation therapy treatments may hinder radiation therapy-initiated anti-tumor immunity, resulting in a relapse of tumor growth in both local and distal areas. This further highlights the importance of immune response in anti-tumor effect of cancer treatments, a factor that cannot be taken into consideration using current xenograft immunodeficient animal models. Note that each of the experiments in this example were repeated at least twice.

Example 5

Radiation-Induced Immune Responses can be Amplied Using an Immunotherapy Agent in Combination with Radiation Therapy This example shows that radiation-induced immune responses can be amplified using an immunotherapy agent, such as Ad-LIGHT™, in combination with radiation therapy. In particular, this example shows that radiation therapy administered in combination with Ad-LIGHT™ immunotherapy can eradicate distant metastases in breast cancer and melanoma. Since current immunodeficient xenograft models could not have provided these results, one of skill will appreciate the need for an immunocompetent xenograft model in view of these results.

Figure 4:
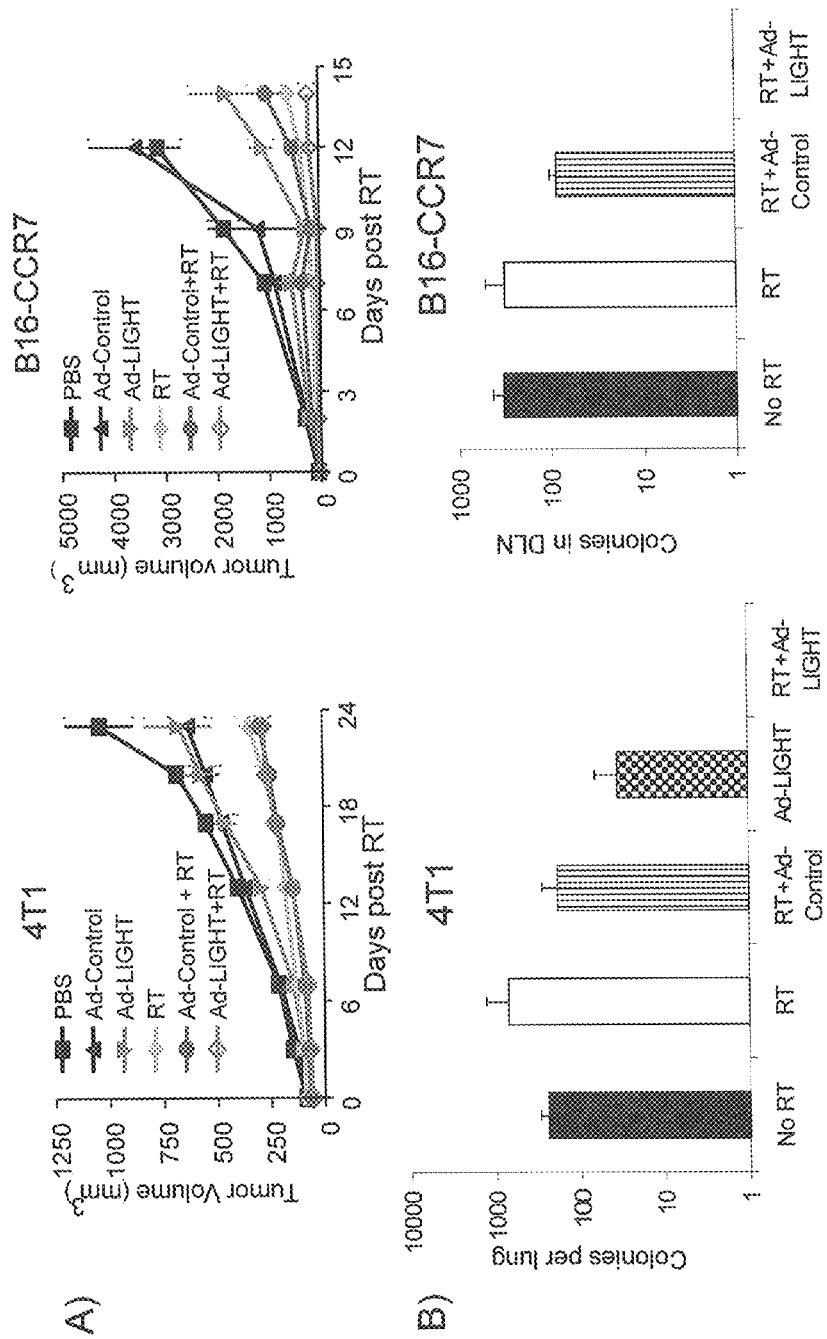
FIGS. 4A through 4C show the effects of tumor growth in the presence of a combination of radiation therapy and Ad-LIGHT™, according to some embodiments.
Figure 4:
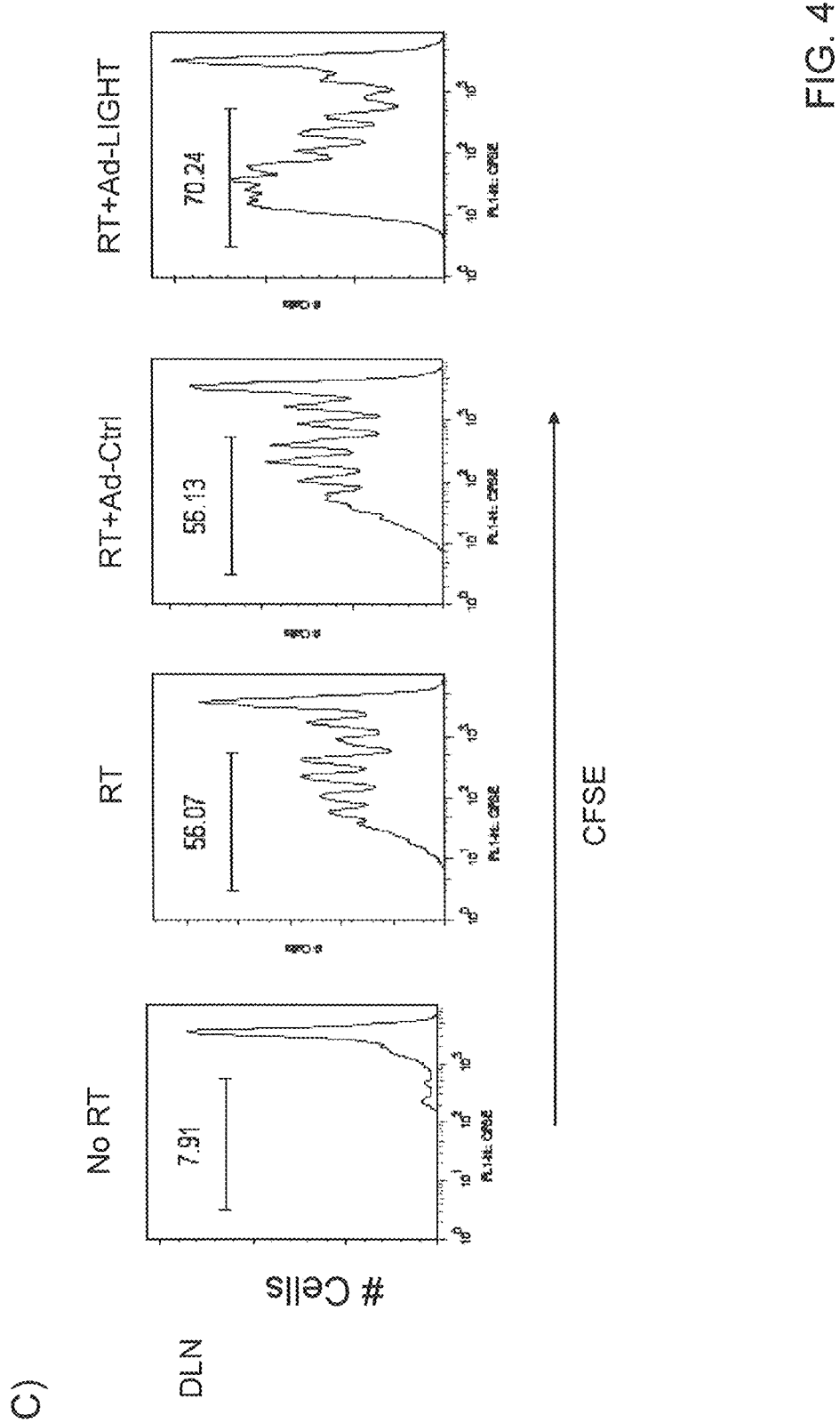

FIGS. 4A through 4C show the effects of tumor growth in the presence of a combination of radiation therapy and Ad-LIGHT™, according to some embodiments. To show the effects of breast tumor growth in the presence of a combination of radiation therapy and Ad-LIGHT™, $1 \times 10^5$ cells of 4T1 breast cancer were injected s.c. into the lower backs of Balb/c mice. The mice received 12 Gy of radiation localized at the tumor on days 14 and 15 after the injection of the cancer cells. A first group of mice received $2 \times 10^{10}$ viral particles of Ad-control (having an Ad-LacZ structure) in 50 μl of PBS by intratumoral injection on days 15 and 16. A second group of mice received $2 \times 10^{10}$ viral particles of Ad-LIGHT™ in 50 μl of PBS by intratumoral injection on days 15 and 16. Note that n=24-41 and results were pooled from 5 experiments.

To show the effects of melanoma tumor growth in the presence of a combination of radiation therapy and Ad-LIGHT™, $1 \times 10^5$ cells of B16-CCR7 melanoma cancer were injected s.c. into the lower backs of C57BL/6 mice. The mice received 12 Gy of radiation localized at the tumor on days 14 and 15 after the injection of the cancer cells. A first group of mice received $2 \times 10^{10}$ viral particles of Ad-control in 50 μl of PBS by intratumoral injection on days 15, 16, and 17. A second group of mice received $2 \times 10^{10}$ viral particles of Ad-LIGHT™ in 50 μl of PBS by intratumoral injection on days 15, 16, and 17. Note that n=6-9 and results were pooled from 2 experiments.

To provide a measure of the efficacy of the combination therapy, the mice received a total of six different treatments for each of 4T1 breast cancer and B16-CCR7 melanoma cancer: (i) only PBS with no adenovirus; (ii) only Ad-control in PBS, (iii) only Ad-LIGHT™ in PBS, (iv) only radiation therapy; and as described above, (v) a combination of radiation therapy and Ad-control, and (vi) a combination of radiation therapy and Ad-LIGHT™. FIG. 4A shows limited local control of tumor growth in mice receiving Ad-LIGHT™ in combination with radiation therapy as compared to mice receiving radiation therapy alone.

To show the effect of the treatment on metastases, the 4T1 and B16-CCR7 tumor cell lines established and treated as above, and on day 25 after the injection of the cancer cells, the tumors were surgically removed. The mice were sacrificed on day 35 for a tumor colonogenic assay, where n=4-5/group. FIG. 4B shows that no colonies were detected in the lungs or the DLN where the radiation therapy was used in combination with the Ad-LIGHT™. The experiments were repeated 3 times.

To show the amplification of radiation therapy-induced immunity that occurs the co-administration of Ad-LIGHT™, $5 \times 10^5$ B16-SIY melanoma cells were injected s.c. into the lower back of mice. On day 17, naïve CD8+ 2C transgenic T-cells were CFSE labeled and then adoptively transferred into B16-SIY tumor-bearing mice. The mice were separated into six groups: (i) a group that did not receive radiation; (ii) a group that received 20 Gy of radiation localized to the tumor; (iii) a group that received 20 Gy of radiation localized to the tumor in combination with $4 \times 10^{10}$ viral particles of Ad-control; (iv) a group that received 20 Gy of radiation localized to the tumor in combination with $4 \times 10^{10}$ viral particles of Ad-LIGHT™; (v) a group that only received $4 \times 10^{10}$ viral particles of Ad-control; and (vi) a group that only received $4 \times 10^{10}$ viral particles of Ad-LIGHT™. DLN were harvested on day 21 to show migration of the T-cells.

FIG. 4C shows that radiation therapy initiates priming of the antigen-specific T-cells. The group receiving radiation therapy has more proliferative T cells than the group that did not receive radiation therapy (p=0.02). And, the combination of radiation therapy and Ad-LIGHT$^m$ markedly amplified the T-cell priming over radiation alone (p=0.02)

Example 6

Adaptive Immunity is Required for Anti-HER2 Mediated Tumor Reduction

This example shows that currently accepted antibody treatments for cancer, such as anti-HER2, can require an adaptive immune system for effectiveness. This is interesting in that the mechanism of action of anti-HER2 is not yet fully understood. Since current immunodeficient xenograft models could not have provided these results, one of skill will appreciate the need for an immunocompetent xenograft model in view of these results.

TUBO mammary cancer cells were injected into Balb/c wild-type mice, and after 3 weeks, most of the mice show a reduced tumor size and diminished tumor mass. Three weeks after the tumor disappeared, these mice were rechallenged by injecting an additional $1 \times 10^6$ TUBO cells, a lethal dose, s.c. into the lower back of the Balb/c mice. No tumors were detected, suggesting that adaptive immunity had occurred.

To determine the effect of adaptive immunity on the efficacy of antibody treatment, a system was created in which no adaptive immunity is possible. neu+ TUBO from Balb/c neu transgenic mice was injected into Balb/c Rag-1 KO mice. On days 18 and 25 after the injection of TUBO, the mice were treated with antibody in the following groups: (i) wild-type Balb/c mice received mIgG (n=7), (ii) wild-type Balb/c mice received aHER2 (n=10), (iii) Balb/c Rag-1 mice received mIgG (n=3), and (iv) Balb/c Rag-1 mice received aHER2 (n=6).

Figure 5:
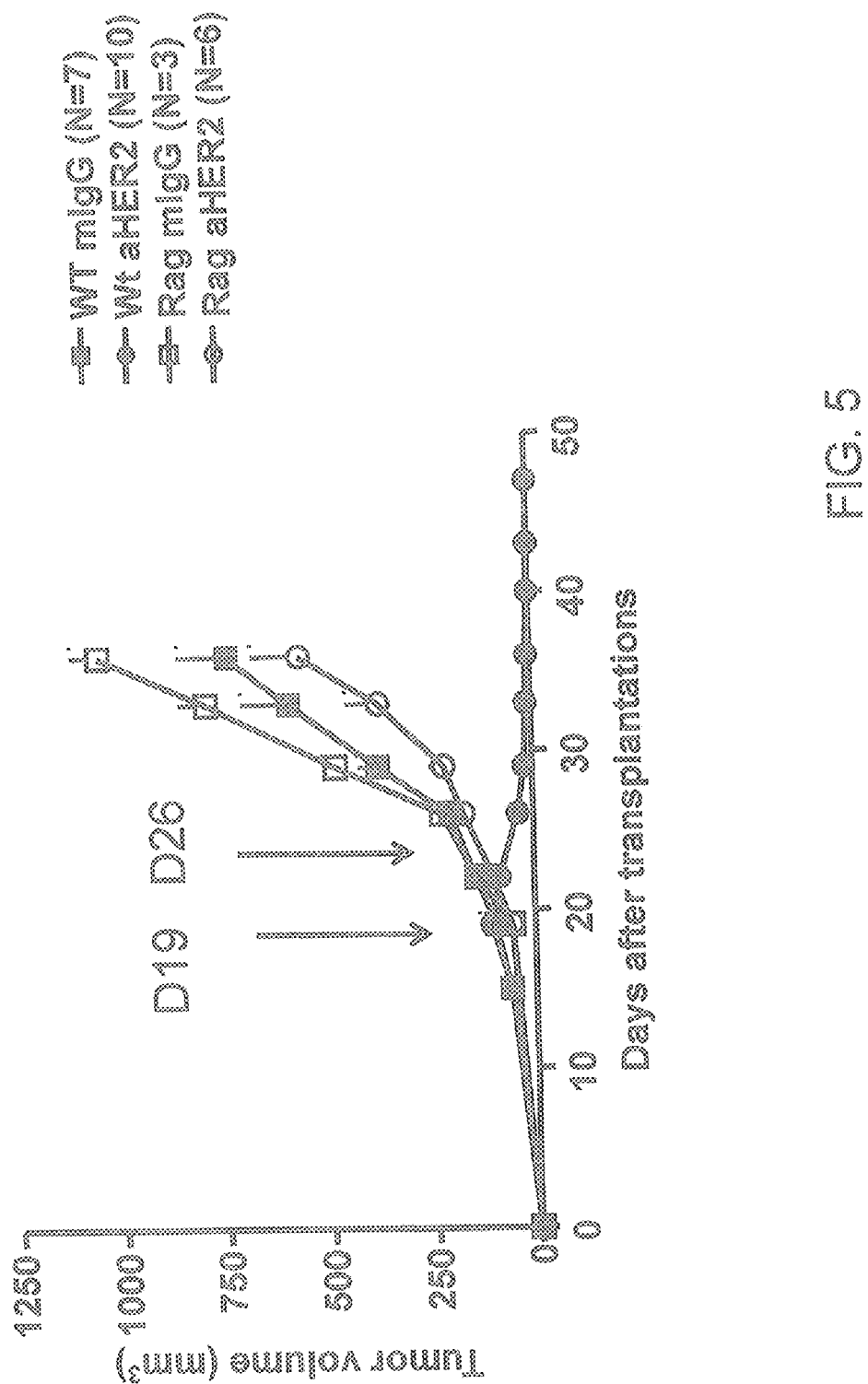
FIG. 5 shows that adaptive immunity is required for anti-HER2 mediated tumor reduction, according to some embodiments.

FIG. 5 shows that adaptive immunity is required for anti-HER2 mediated tumor reduction, according to some embodiments. Wild-type mice having an immune system were able to develop an adaptive immunity to the TUBO, whereas the Rag-1 mice have no immune system and could not develop an adaptive immunity. The wild-type mice receiving mIgG did not show a substantial reduction in tumor volume, whereas wild-type mice receiving 80 μg/kg anti-HER2 on each of days 19 and 26 after the TUBO injection did show an eradication of the tumors. The Rag-1 mice did not show a similar decrease in tumor size, even in the presence of aHER2. Accordingly, the presence of lymphocytes is essential to aHER2 treatment, and an immunocompetent xenograft model would be appreciated by one of skill in testing the efficacy of antibody therapies, such as aHER2.

To determine the importance of T-cells in the efficacy of aHER2, anti-CD4 and anti-CD8 were administered to mice having TUBO cells to deplete the respective T-cells. $1 \times 10^6$ TUBO cells were injected into Balb/c mice. After the tumors were well-established, the mice were separated into groups subject to the following groups of treatments: (i) PBS only, (ii) aHER2 in PBS, (iii) aHER2 and anti-CD8 in PBS, (iv) aHER2, anti-CD4, and anti-CD8 in PBS. The anti-CD4 and anti-CD8 antibodies were administered in amounts of 100 μg each at 10 days, 17 days, 24 days, and 41 days after tumor injection. The aHER2 was administered in an amount of 100 μg on day 10, 200 μg on day 17, 100 μg on day 24, and 200 μg on day 41.

Figure 6:
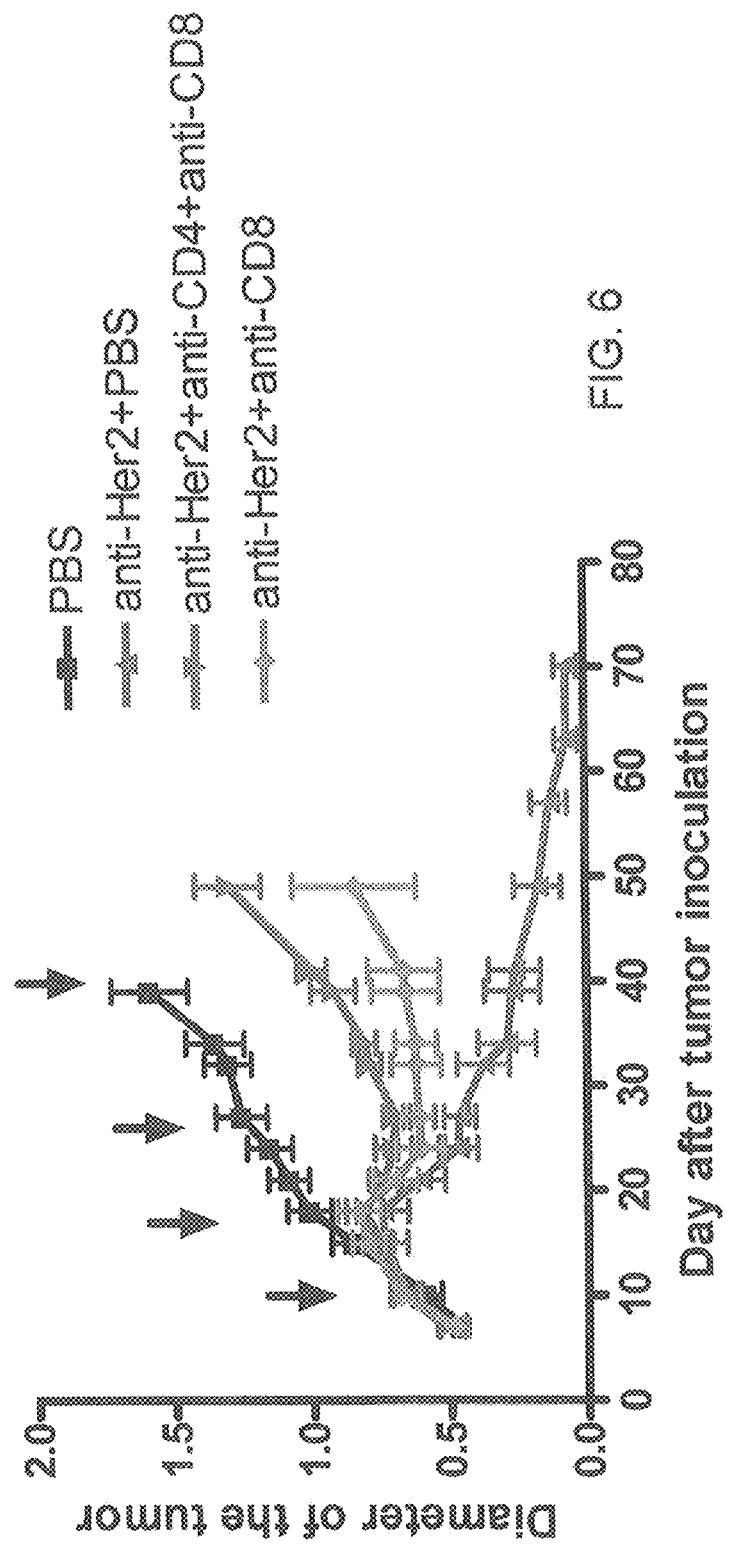
FIG. 6 shows that T-cells are essential to the action of aHER2 in TUBO cell treatment, according to some embodiments.

FIG. 6 shows that T-cells are essential to the action of aHER2 in TUBO cell treatment, according to some embodiments. The aHER2 without any T-cell depletion showed the best results, whereas depletion of T-cells using anti-CD8 resulted in some slowing of tumor growth, but the tumor soon regrew. The depletion of T-cells using anti-CD4 and anti-CD8 showed results that were even more dramatic. Depletion of CD8 leaded to a resurge of tumor growth in 1-2 weeks.

Combination therapy of aHER2 and a chemotherapeutic could show the same reduction in efficacy due to the immunosuppressive action of the chemotherapeutic. To show this, $1 \times 10^6$ TUBO cells were injected into Balb/c mice. After the tumor was well-established, the mice were separated into groups subject to the following groups of treatments: (i) 80 μg mIgG only, (ii) 80 μg aHER2 only, (iii) 5 mg/kg DOXORUBICIN only, (iv) 15 mg/kg DOXORUBICIN only, (v) a combination of 80 μg aHER2 and 5 mg/kg DOXORUBICIN, and (vi) a combination of 80 μg aHER2 and 15 mg/kg DOXORUBICIN. The antibodies and chemotherapeutic were administered intratumorally, the time injections and tumor size measurements were taken at 19 and 26 days after tumor injection.

Figure 7:
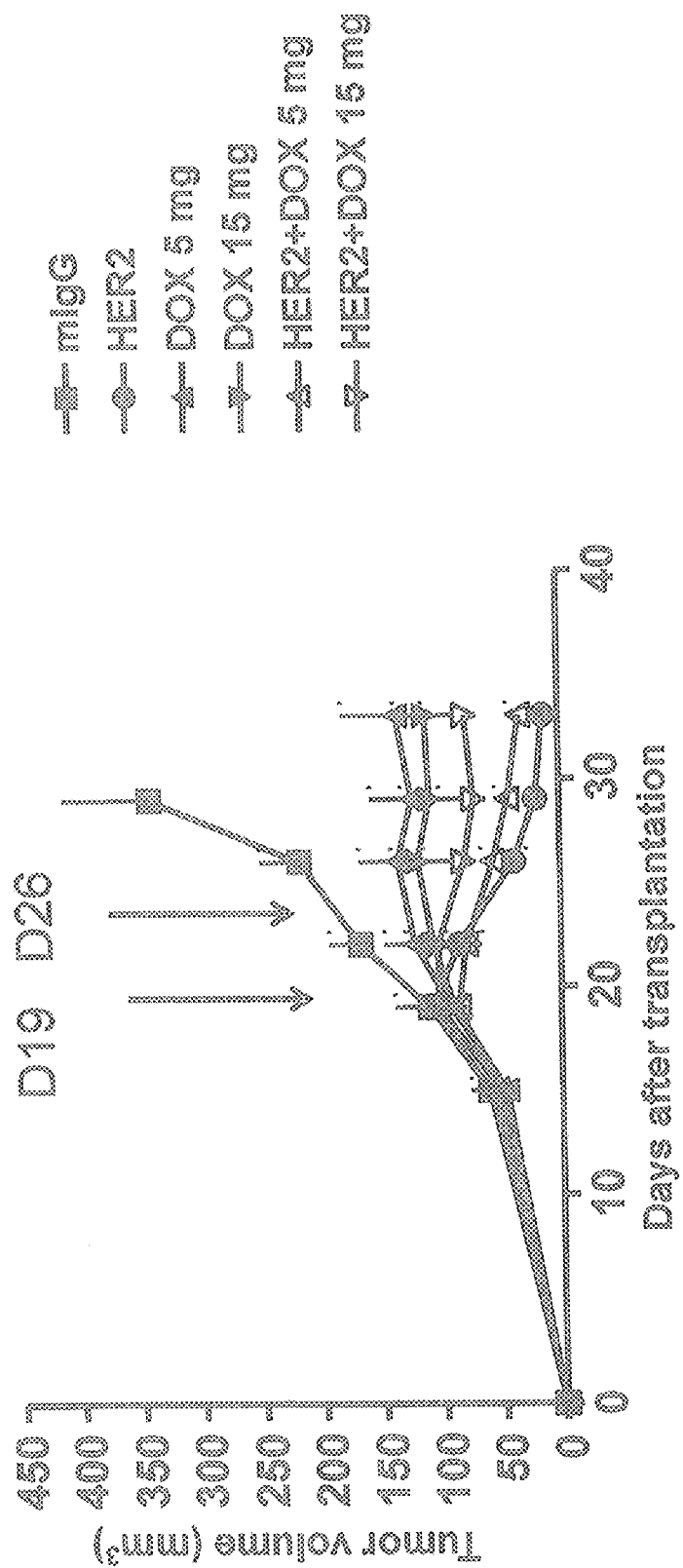
FIG. 7 shows that administration of a chemotherapeutic agent can reduce the efficacy of aHER2, according to some embodiments.

FIG. 7 shows that administration of a chemotherapeutic agent can reduce the efficacy of aHER2, according to some embodiments. The aHER2 alone reduces tumor volume substantially, but the combination of aHER2 with DOXORUBICIN. Interestingly, although DOXORUBICIN reduces tumor burden alone, the lower dose of DOXORUBICIN with aHER2 reduces the tumor size more than the higher dose of DOXORUBICIN with aHER2. In fact, aHER2 shows the most tumor reduction and adding the DOXORUBICIN reduces the efficacy of the aHER2 and allows regrowth of the tumor.

The efficacy of aHER2 is dependent on immune response. Accordingly, the presence of an immune response can be essential to antibody treatment, and an immunocompetent xenograft model would be appreciated by one of skill in testing the efficacy of antibody therapies, particularly in combination with other therapies that may suppress immune response.

Example 7

Combination Administration of Ad-LIGHT$^m$ and aHER2 Provide a Synergistic Response to Reduction of TUBO Tumors This example shows that combination therapies that affect or depend on immune response can be tested using an immunocompetent xenograft model to enable one of skill to identify synergies. In such systems, one of skill would appreciate an immunocompetent xenograft model.

When tumors are well-established, the effect of anti-neu antibodies and Ad-LIGHT$^m$ on tumor reduction diminishes. Once anti-neu antibody is discontinued, TUBO tumors will regrow in about 3-4 weeks (data not shown). T establish whether the combination of Ad-LIGHT$^m$ and aHER2 is effective against establish TUBO tumors, $1 \times 10^6$ TUBO tumor cells were injected to Balb/c mice s.c. After the tumor was well-established, $1 \times 10^{10}$ viral particles of Ad-LIGHT$^m$ or Ad-LacZ was injected intratumorally on day 18 after tumor injection. The antibodies, aHER2 and Isotype IgG, were injected in an amount of 50 μg i.p. on day 18 and 25 after injection of the tumor. The combination treatment was also administered on days 18 and 25. The mice were separated into groups subject to the following groups of treatments: (i) Ad-LIGHT$^m$ only, (ii) aHER2 only, (iii) Isotype IgG only, (iv) Ad-LIGHT$^m$ in combination with aHER2, and (v) Ad-LacZ in combination with aHER2.

Figure 8:
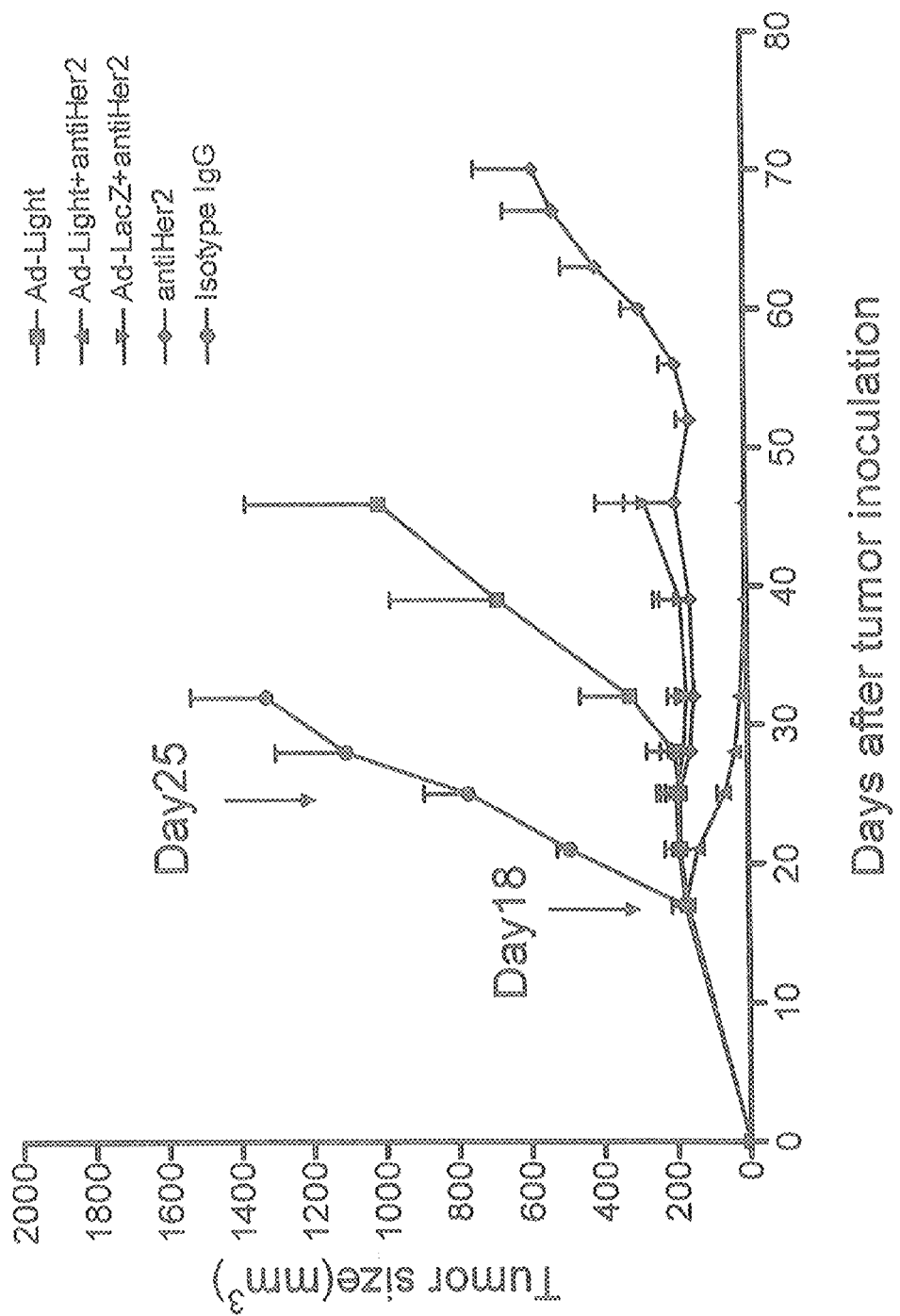
FIG. 8 shows combination administration of Ad-LIGHT™ and aHER2 provide a synergistic response to reduction of TUBO tumors, according to some embodiments.

FIG. 8 shows combination administration of Ad-LIGHT'" and aHER2 provide a synergistic response to reduction of TUBO tumors, according to some embodiments. It can also be seen that each group reduces tumor size substantially when compared with isotype IgG group after day 21. The Ad-LIGHT'" and anti-HER2 combination reduces tumor size significantly when compared with either ad-LIGHT alone or anti-Her2 alone after day 25 ($p<0.05$). The statistic analysis, in this example, was performed with two-tail student's t test.

Impressively, no tumor could be detected after the combination therapy, while tumors grow progressively wither aHER2 or Ad-LIGHT'" alone. Similar to local radiation therapy, anti-neu antibodies can reduce tumor burden, and they can also potentiate LIGHT-mediated immunity. Given the results provided herein, it is contemplated that radiation therapy can also potentiate LIGHT-mediated immunity to anti-HER2. Further, it is believed that the radiation therapy has broader applications, since it can be used with any solid tumor. Accordingly, the presence of an immune response can be essential to combination therapies, and an immunocompetent xenograft model would be appreciated by one of skill in testing the efficacy of such therapies, particularly if it is suspected that such therapies depend on immune response.

Example 8

The Immunocompetent Xenograft Model—Design and Proof of Concept

This example provides a solution to the long-felt and unsolved need for an immunocompetent xenograft model to evaluate therapies, such as those discussed above. An example of the problems presented through the use of immunodeficient xenograft models are illustrated in at least the examples above.

To address these problems, an immune system was reconstituted in an immunodeficient animal by injecting a desired composition of T-cells into the immunodeficient animal. It was discovered that a preselected number of responsive T-cells can be integrated with a preselected number of non-responsive T-cells to control the homeostatic proliferation of the reactive T-cells. In fact, the homeostatic proliferation of responsive T-cells can be controlled in immunodeficient animals, allowing for the reconstitution of an immune system by controlling the number and ratio of responsive T-cells to nonresponsive T-cells.

Figure 9:
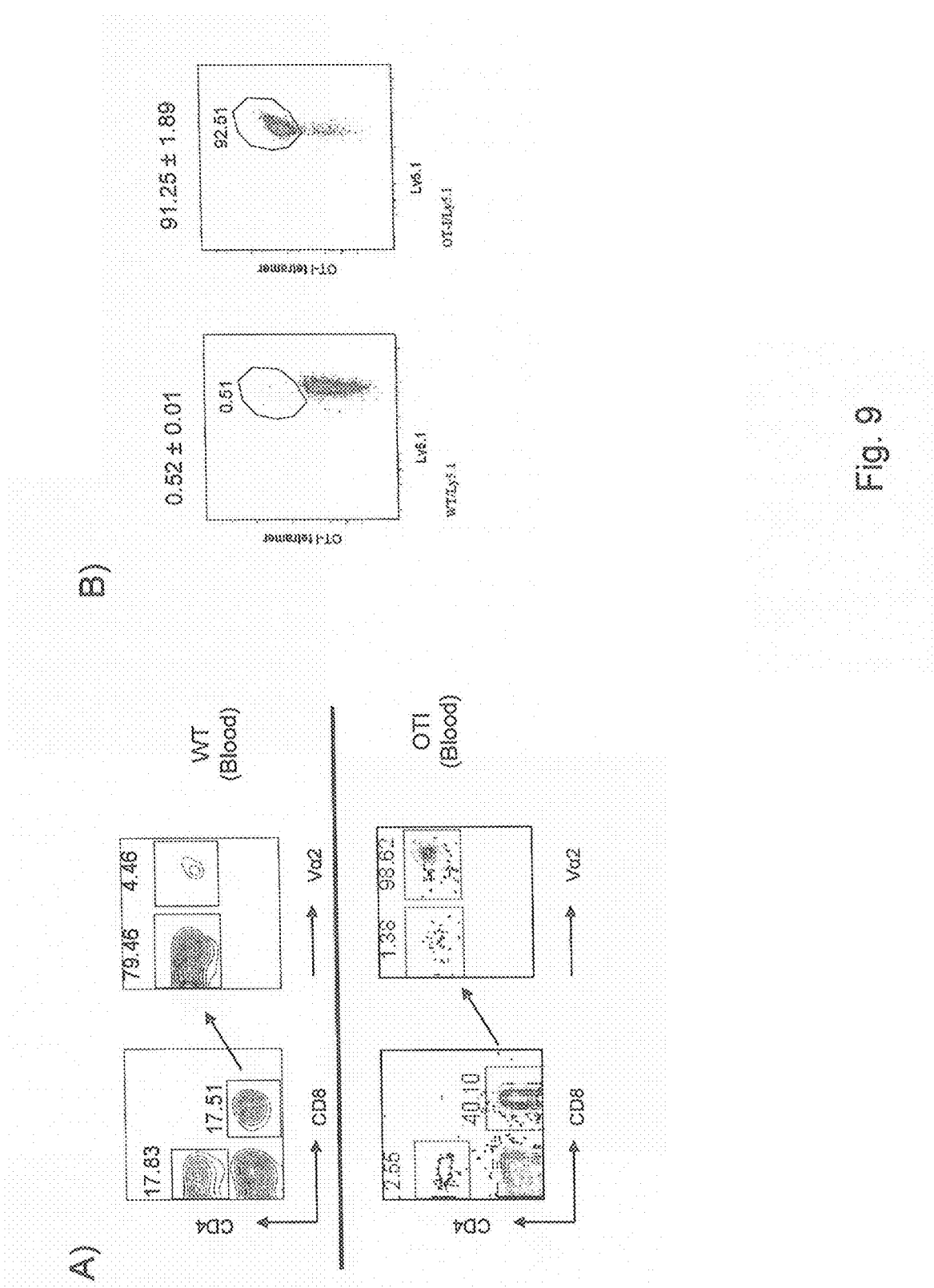
FIGS. 9A and 9B compare ratios of responsive T-cells to non-responsive T-cells in wild-type mice to ratios of responsive T-cells to non-responsive T-cells in OT-1 transgenic mice, according to some embodiments.

FIGS. 9A and 9B compare ratios of responsive T-cells to non-responsive T-cells in wild-type mice to ratios of responsive T-cells to non-responsive T-cells in transgenic mice, according to some embodiments. The transgenic mice are transgenic TCR mice, and more specifically, OT-1 transgenic mice. The OT-1 transgenic mice have T-cells that are highly OVA reactive but non-tumor reactive. FIG. 9A compares the counts of responsive and non-responsive T-cells in wild-type mice to those counts in OT-1 transgenic mice. The lymphocytes in the blood of the OT-1 mice contain more than 98% OT-1 T-cells. FIG. 9B shows that the splenocytes from adult OT-1 transgenic mice (6-8 weeks of age) were stained to show OT-1-tetramer (SINFIKEL peptide+class 1 tetramer) and LY5.1. More than 91% of the OT-1 T-cells were detected in the CD8+ T-cells. Accordingly, about 91% to about 98% of the CD8+ T-cells taken from OT-1 transgenic mice are antigen-specific T-cells for OVA and cannot respond to antigens from human tumors. However, these cells do inhibit homeostatic proliferation of responsive cells. About 1% of the remaining non-OT-1 T-cells can potentially respond to human tumor cell antigens. In fact, without intending to be limited by any theory or mechanism of action, the number of such tumor-reactive T-cells is believed to be about 5% of that 1%, or about 0.05% of the remaining non-OT-1 T-cells.

Figure 10:
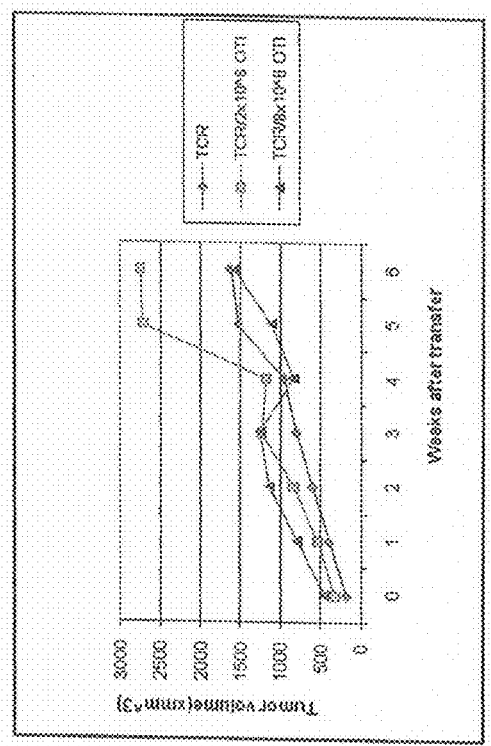
FIGS. 10A and 10B show that established human tumors are rejected by T-cells from wild-type mice by not by T-cells from OT-1 transgenic mice, according to some embodiments.
Figure 10:
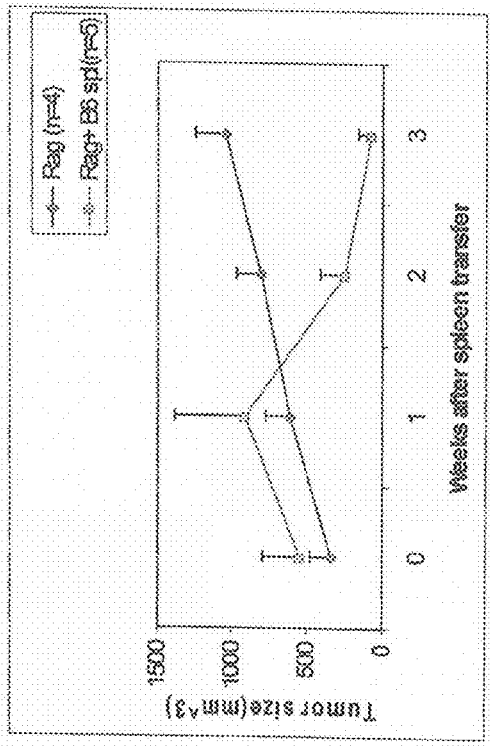

FIGS. 10A and 10B show that established human tumors are rejected by T-cells from wild-type mice by not by T-cells from OT-1 transgenic mice, according to some embodiments. To determine the correct number and ratio of responsive T-cells and non-responsive T-cells that would be needed to avoid xenograft rejection, the number and ratio was varied in mice in an effort to simulate the approximate number of tumor reactive T-cells in human patients. Human lung tumor cells, A549 human alveolar basal epithelial cells, were injected s.c. into B6Rag-1 −/− mice. The tumors were allowed to establish for about 3 weeks to about 4 weeks. The mice received $2 \times 10^6$ total LN cells by adoptive transfer from wild-type mice, of which one million are T-cells and about 1% of those T-cells were expected to be tumor-reactive, meaning that about 10,000 of the total number of T-cells were considered as responsive to the xenograft. Tumor growth was monitored for 3 weeks.

FIG. 10A shows that the xenograft tumor was rejected by when the T-cells used to reconstitute the immune system were obtained from wild-type mice. In subsequent experiments, however, mice receiving from about $2 \times 10^6$ to about $8 \times 10^6$ total LN cells by adoptive transfer from OT-1 transgenic mice, each transfer of which having about from about 500 responsive cells to about 2000 responsive cells, respectively, carried sustainable xenografts that were not rejected over a three month period. FIG. 10B shows that the established A549 human lung tumor continued to grow in the OT-1 transgenic mice with the transferred OT-1 SP/LN cells. Tumor growth was monitored for 6 weeks.

It was estimated that, in some embodiments, the immunocompetent model can have about 300 to about 3000 T-cells that are tumor reactive, which is close to the amount estimated for human T-cells that respond to human tumor antigens in a given patient.

Example 9

The Immunocompetent Xenograft Model—Actual Use to Test the Dependence of the Efficacy of Radiation Therapy on Immune Response The A549 lung tumor is believed to be resistant to radiation due to studies performed in immunodeficient xenograft models. Surprisingly, this example shows that radiation therapy does, in fact, reduce the size of A549 lung tumors in an immunocompetent xenograft model.

Immunocompetent xenograft models produced using the procedure of FIG. 10B received 20 Gy of radiation therapy three days after the reconstitution of the immune system. The mice were tested using the following treatment groups: (i) control mice receiving only the xenograft, such that the immune system was not reconstituted; (ii) mice receiving the xenograft and reconstituted immune system; (iii) mice receiving the xenograft and radiation therapy; and (iv) mice receiving the xenograft, a reconstituted immune system, and radiation therapy.

Figure 11:
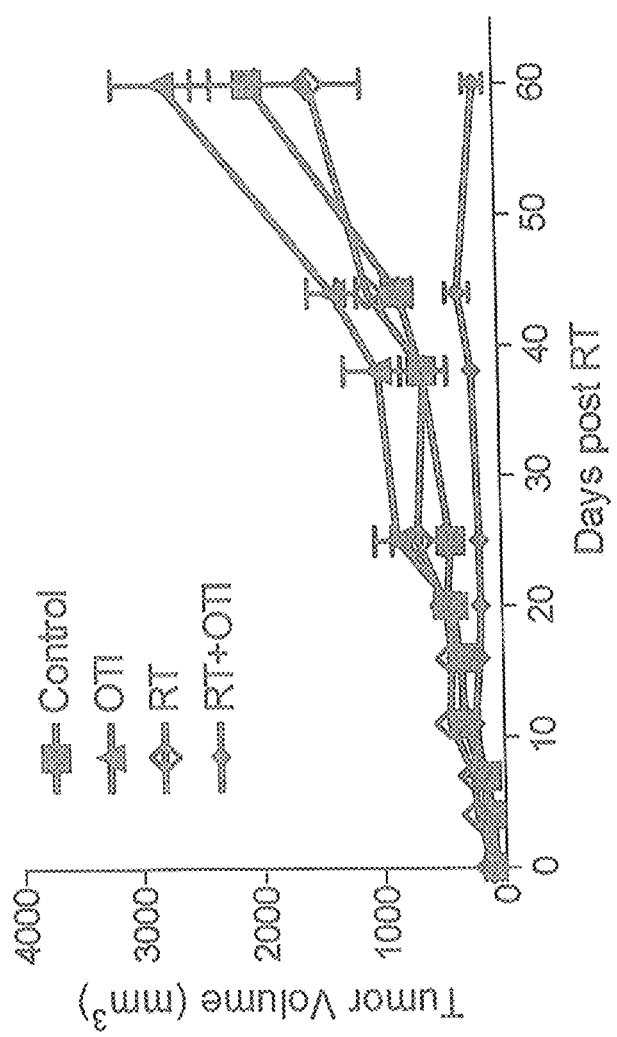
FIG. 11 shows that a tumor that appears resistant to radiation in an immunodeficient xenograft model has a substantial reduction in size when assayed in an immunocompetent xenograft model, according to some embodiments.

FIG. 11 shows that a tumor that appears resistant to radiation in an immunodeficient xenograft model has a substantial reduction in size when assayed in an immunocompetent xenograft model, according to some embodiments. The immunodeficient xenograft model did not show a significant difference in tumor size with radiation therapy alone ($p=0.48$), and reconstitution of the immune system did not improve results in the absence of radiation therapy ($p=0.3$).

The immunocompetent xenograft model, however, showed a substantial reduction in size (*p=0.018 at day 60). Clinical uses of radiation therapy are usually followed by chemotherapy, a treatment that has been shown in the examples herein to affect immune response, making the radiation therapy perform moreso as it does in immunodeficient xenograft models.

Accordingly, the immunocompetent xenograft model shows that radiation therapy is a powerful treatment for even a radiation-resistant tumor such as the A549 lung tumor. It is likely that the effect on radiation-sensitive tumors will be even more profound when observed in models having competent immune systems, suggesting that some conditions may be better treated with a modification of current treatment regimes that reflects the more accurate immunocompetent xenograft model. In some embodiments, for example, radiation therapy can be used to induce a strong immune response to enhance the reduction of an established tumor.

I claim:

1. An immunocompetent mouse model, comprising:
   an immunodeficient mouse modified to have a reconstituted immune system; and,
   a xenograft transplanted in the immunodeficient mouse and allowed to establish for an establishment period of at least about 10 days, the xenograft simulating a tissue in a subject in need of a treatment;
   wherein,
   the reconstituted immune system is created after the establishment period;
   the reconstituted immune system is created by administering to the immunodeficient mouse a total number of T cells from a donor transgenic mouse that expresses a transgene encoding a non-xenograft specific T-cell receptor (TCR), wherein the total number of T-cells consists of a preselected number of potentially responsive T-cells, a preselected number of non-responsive T-cells, and a preselected ratio of potentially responsive T-cells to total T-cells;
   the preselected number of potentially responsive T-cells simulates a number of potentially responsive T-cells in the subject and
   the ratio of the number of potentially responsive T-cells to total T-cells ranges from about 1:100,000 to about 30:100,000; and
   wherein rejection of the xenograft is inhibited relative to when the immune system of the immunodeficient mouse is reconstituted with T-cells from a wild type mouse.

2. The immunocompetent mouse model of claim 1, wherein the mouse is a Rag-1 immunodeficient mouse.

3. The immunocompetent mouse model of claim 1, wherein the mouse is a C57BL/6 immunodeficient mouse.

4. The immunocompetent mouse model of claim 1, wherein the xenograft simulates a solid human cancer in the subject.

5. The immunocompetent mouse model of claim 1, wherein the xenograft simulates a liquid human cancer in the subject.

6. The immunocompetent mouse model of claim 1, wherein the xenograft comprises a cancer tissue selected from the group consisting of breast cancer, lung cancer, prostate cancer, colon cancer, renal cancer, liver cancer, leukemia, lymphoma, and skin cancer.

7. The immunocompetent mouse model of claim 1, wherein the xenograft comprises a donor tissue.

8. The immunocompetent mouse model of claim 1, wherein the xenograft comprises a donor tissue selected from the group consisting of heart tissue, lung tissue, kidney tissue, liver tissue, pancreas tissue, intestinal tissue, hand tissue, cornea tissue, skin graft tissue, penis tissue, blood vessel tissue, and bone tissue.

9. The immunocompetent mouse model of claim 1, wherein the establishment period ranges from about 2 weeks to about 4 weeks.

10. The immunocompetent mouse model of claim 1, wherein the establishment period is about 3 weeks.

11. The immunocompetent mouse of claim 1, wherein the number of potentially responsive T-cells ranges from about 50 to about 5000.

12. The immunocompetent mouse model of claim 1, wherein the number of potentially responsive T-cells ranges from about 200 to about 2000.

13. The immunocompetent mouse model of claim 1, wherein the ratio of potentially responsive T-cells to total T-cells ranges from about 1:100,000 to about 10:100,000.

14. The immunocompetent mouse model of claim 1, wherein the potentially responsive T-cells comprise T-cells from a donor OT-1 transgenic TCR mouse that expresses a transgene encoding a non-xenograft specific TCR.

15. The immunocompetent mouse model of claim 1, wherein the potentially responsive T-cells comprise CD8+ 2C transgenic T-cells.

16. An immunocompetent mouse model comprising:
   an immunodeficient mouse modified to have a reconstituted immune system with a simulated T-cell response from exogenously-derived cells obtained from a transgenic mouse that expresses a transgene encoding a non-xenograft specific T-cell receptor (TCR); and,
   a xenograft transplanted in the immunodeficient mouse and allowed to establish for an establishment period of at least about 10 days,
   the xenograft simulating a tissue in a subject in need of a treatment;
   wherein,
   the reconstituted immune system is created after the establishment period through the administration of an effective amount of the exogenously-derived cells that provides the simulated T-cell response in the otherwise immunodeficient mouse;
   the exogenously-derived cells comprise a preselected number of potentially responsive T-cells, a preselected number of non-responsive T-cells, and a preselected ratio of potentially responsive T-cells to total T-cells;
   the preselected number of potentially responsive T-cells simulates a number of potentially responsive T-cells in the mouse, and
   the ratio of the number of potentially responsive T-cells to total T-cells ranges from about 1:100,000 to about 30:100,000; and
   wherein rejection of the xenograft is inhibited relative to when the immune system of the immunodeficient mouse is reconstituted with T-cells from a wild type mouse.

* * * * *